United States Patent
Auestad et al.

(10) Patent No.: US 6,495,599 B2
(45) Date of Patent: Dec. 17, 2002

(54) INFANT FORMULAS CONTAINING LONG-CHAIN POLYUNSATURATED FATTY ACIDS AND USES THEROF

(75) Inventors: Nancy Auestad, Columbus, OH (US); Russell J. Merritt, Columbus, OH (US); Deborah L. O'Connor, North York (CA)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/821,010

(22) Filed: Mar. 30, 2001

(65) Prior Publication Data

US 2002/0004527 A1 Jan. 10, 2002

Related U.S. Application Data

(60) Provisional application No. 60/196,970, filed on Apr. 13, 2000.

(51) Int. Cl.[7] .............................................. A16K 31/20
(52) U.S. Cl. ........................................................ 514/560
(58) Field of Search ......................................... 514/560

(56) References Cited

U.S. PATENT DOCUMENTS

| | | | |
|---|---|---|---|
| 4,670,285 A | 6/1987 | Clandinin | 426/602 |
| 5,374,657 A | 12/1994 | Kyle et al. | 514/547 |
| 5,550,156 A | 8/1996 | Kyle et al. | 514/547 |
| 5,658,767 A | 8/1997 | Kyle et al. | 514/560 |
| 6,036,992 A | 3/2000 | Dohnalek et al. | 426/662 |
| 6,294,206 B1 * | 9/2001 | Barret-Reis et al. | 426/72 |
| 6,297,279 B1 * | 10/2001 | Wang et al. | 514/560 |

FOREIGN PATENT DOCUMENTS

| | | |
|---|---|---|
| EP | 0484226 | 5/1992 |
| EP | 0957173 | 9/1999 |
| WO | WO 98/36745 | 8/1998 |
| WO | WO98/44917 | 10/1998 |

OTHER PUBLICATIONS

Boehm, et al., "Docosahexaenoic and Arachidonic Acid Absorptin in Preterm Infants Fed LCP–Free or LCP–Supplemented Formula in Comparison to Infants Fed Fortified Breast Milk", Ann Nutr Metab 1997; 41:235–241.

Clandinin, et al., "Assessment of the Efficacious Dose of Arachidonic and Docosahexaenoic Acids in Preterm Infant Formulas: Fatty Acid Composition of Erythrocyte Membrane Lipids", Pediatric Research, vol. 42, No. 6, 1997, pp. 819825.

Abstract: Efficiency of Dietary Long–Chain Polyunsaturated Fatty Acids (LCP) For Preterm (PT) Infants, Neuringer et al, Experimental Biology 2000.

Abstract: Evaluation of Long–Chain Polyunsaturated Fatty Acid (LCP) Containing Formulas for Preterm (PT) Infants, Connor et al, Experimental Biology 2000.

Abstract: Growth Tolerance an Morbidity of Preterm Infants Fed Exclusively Human Milk, Exclusively Preterm Infants Formulas or a Combination of Human Milk and a Preterm Infant Formula Until Term Corrected Age (CA), O'Connor et al.

Two Essential Nutrients, DHA and AA, Found to Significantly Improve Mental Development of Infants, Business Wire, Mar. 7, 2000.

A randomized controlled trial of early dietary supply of long–chain polyunsaturated fatty acids and mental development in term infants, Birch et al, Developmental Medicine & Child Neurology 2000, 42:174–181.

Development of low–birthweight infant at 19 months of age correlates with early intake and status of long–chain polyunsaturated fatty acids, Woltil et al, Prostaglandins, Leukotrienes and Essential Fatty Acids (1999) 61(4), 235–241.

Visual evoked potentials and dietary long chain polyunsaturated fatty acids in preterm infants, Fladella et al, Archieves of Disease in Childhood 1996; 75:F108–F112.

Improved Growth of Very Low Birthweight Infants, Friel et al, Nutrition Research, vol. 13, pp. 611–620, 1993.

Evaluation of Long–Chain Polyunsaturated FattyAcid Supplemented Formula on Growth, Tolerance and Plasma Lipids in Preterm Infants up to 48 Weeks Postconceptional Age, Vanderhoof et al, Journal of Pediatric Gastroenteroglogy and Nutrition 29:318–326, Sep. 1999.

Effect of DHA–Containing Formula on Growth of Preterm Infants to 59 Weeks Post menstrual Age, Ryan et al, American Journal of Human Biology 11:457–487 (1999).

Long–Chain polyunsaturated fatty acid status and early growth of low birth weight infants, Woltil et al, Eur J Pediatr (1998) 157: 146–152.

Intestinal absorption of long–chain polyunsaturated fatty acids in preterm infants fed breast milk or formula, Carnielli et al, Am J Clin Nutr 1998; 67:97–103.

(List continued on next page.)

Primary Examiner—Kevin E. Weddington
(74) Attorney, Agent, or Firm—Thomas D. Brainard

(57) ABSTRACT

Methods for providing nutrition and for enhancing neurological development of preterm infants are disclosed. Also disclosed is an improved nutritional composition containing specified amounts of DHA and AA as well as their precursor essential fatty acids alpha-linolenic and linoleic acids. The methods involve feeding LCP supplemented, nutrient-enriched formulas for an extended feeding regimen, typically until at least 3 months corrected age (CA), preferably to 6 or even 12 months CA. The neurological developments, for example, visual development, motor development and language development were enhanced without findings of anthropometric growth faltering or inhibition.

45 Claims, 2 Drawing Sheets

OTHER PUBLICATIONS

Figure 1A:
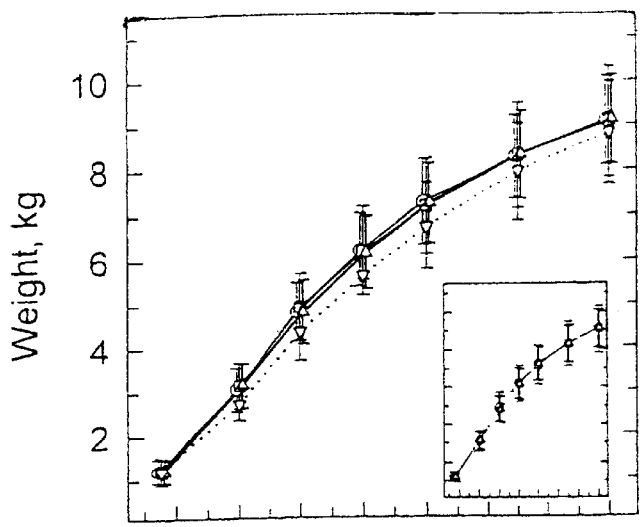

Docosahexaenoic Acid plus Arachidonic Acid Enhance preterm Infant, Hansen et al, Protaglandins, Leukotrienes, and Essential Fatty Acids, Hansen et al, V.57 196–0952–3278 1997 (T16).

Effect of long –chain n–3 fatty acid supplementation on Visual acuity and growth of preterm infants with and without bronchopulmonary dysplasia, Carlson et al, Am J Clin Nutr 1996; 63:687–97.

The Very Low Birth Weight Premature Infant Is Capable of Synthesizing Arachidonic and Docosahexaenoic Acid from Linoleic and Linolenic Acids, Carnnielli et al, Pediatric Research, vol. 40 No. 1 1996.

Influence of feeding artificial–formula milks containing docosahexaenoic and arachidonic acids on the postnatal long–chain polyunsaturated fatty acid status of healthy preterm infants, Forman–Van Drongelen et al, British Journal of Nutrition (1996), 76, 649–667.

Docosahexaenoic and arachidonic acid content of serum and red blood cell membrane phospholipids of preterm infants fed breast milk, standard formula or formula supplement with n–3 and n–6 long–chain polyunsaturated fatty acids, Boehm et al, Eur J Pediatric (1996) 155: 410–416.

Stereospecific Analysis of Triacylglycerols Rich in Long–Chain Polyunsaturated FattyAcids, Myher et al, Lipids, vol. 31, No. 2 (1996).

A randomized Trial of visual Attention of Preterm Infants Fed Docosahexaenoic Acid Until Nine Months, Carlson et al, Lipids, vol. 31, No. 1 (1996).

A Randomized Trail of Visual Attention of Preterm Infants Fed Docosahexaenoic Acid Until Two–Months, Carlson et al, Lipids, vol. 31, No. 1 (1996).

Arachidonic acid status correlates with first year growth of preterm infants, Carlson et al, Proc Natl Acad Sci USA 1993b:90:1073–1077.

The Role of PUFA in infant nutrition, INFORM, vol. 6, No. 8 (Aug. 1995).

Growth and Development of Premature Infants in Relation to w3 and w6 Fatty Acid Status, Carlson et al, Fatty Acids and Lipids: Biological Aspects, World Rev Nut Diet, Basel Karger, 1994 vol. 75, pp. 63–39.

Visual–acuity development in healthy preterm infants: effect of Marine–oil supplementation 1–3, Carlson et al, Am J Clin Nutr 1993; 58:35–42.

First Year Growth of Preterm Infants Fed Standard Compared to Marine Oil n–3 Supplemented Formula, Carlson et al, LIPIDS, vol. 27, No. 11 1992 pp. 901–907.

Effect of vegetable and marine oils in preterm infant formulas on blood arachidonic and docosahexaenoic acids, Carlson et al., Journal of Pediatrics, vol. 120 No. 4 part 2 S159–S186.

Essentiality of w3 Fatty Acids in Growth and Devleopment of Infants, Carlson et al, Health Effects of w3 Polyunsaturated Fatty Acids in Seafoods, World Rev Nut Diet Base Karger 1991, vol. 66, pp. 74–86.

Arachidonic an docosahexaenoic acids are biosynthesized from their 18–carbon precursors in human infants, Salem et al, Proc Natl Acad Sci USA , vol. 93 pp. 49–54, Jan. 1996.

Lipid Requirements of VLBW Infants for Optimal Growth and Developemnt, in Lipds, Learning and the Brain; Fats in Infant Formula, Report of the 103rd Ross Conference on Pediatric Research, Chapter 18 pp. 188–214, Columbus, OH Ross Laboratories, 1993c.

Intrauterine fatty acid accretion rates in human brain: implications for fatty acid requirements. Clandinin et al, Early Human Dev. 1980:4/2:121–9.

Visual evoked poential (VEP) etimates of spatial acuity in 4–month old infants: A new swept–parameter technique, Hartmann et al, Vision Science and Its Applications: Technical Digest Series, vol. 1, 1998.

Safety and efficacy of Omega–3 fatty acids in the nutrition of very low birth weight infants: Soy oil and marine oil supplementation of formula, Uauy et al, The Journal of Pediatrics, vol. 124, No. 4, pp. 612–620 Apr. 1994.

Breast–Feeding and Optimal Visual Development, Birch et al, J Pediatr Ophthalmol & Strabismus 1993: 30:33–38.

Effects of supplementation of w3 long–chain polyunsaturated fatty acids on retinal and cortical development in premature infants, Hoffman et al, Am J Clin Nutr 1993; 57:807S–12S.

Visual and brain function measurements in studies of n–3 fatty acid requirements of infants, Uauy et al, Journal of Pediatrics Apr. 1992, vol. 120 No. 4 part 2, pp. S168–S186.

Essentiality of Dietary w3 Fatty Acids for Premature Infants: Plasm and Red Blood Cell Fatty Acid Composition1, Hoffman et al, LIPIDS vol. 27 No. 11 1992.

Retinal and Cortical Function of Very Low Birthweight Infants at 36 and 37 weeks Postconception, Birch et al, Clin Vision Sci vol. 5, No. 4 pp. 363–373 1990.

Effect of Dietary Omega–3 Fatty Acids on Retinal Function of Very–Low–Birth–Weight Neonates 1, Uauy et al, Pediatric Research, vol. 28 No. 5, 1990.

Abstract: Growth of Preterm Infants Fed Nutrient Enriched or Term Formula After Hospital Discharge, Carver et al, Pediatric Academi Societies & American Academy of Pediatrics Joint Meeting 2000.

Abstract: 4904.B514 Longtitudinal VEP Measures of Contrast Sensitivity in Full–Term Human Infants Fed Different Dietary Fatty Acids Fitzgerald et al, Investigative Ophthalomology & Visual Science, Feb. 15, 1996, vol. 37, No. 3.

Abstract: 2437.B282 Relationships between visual acuity and visual attention measures in rhesus monkey infants, Neuringer et al, Investigative Ophthalmology & Visual Science, Feb. 15, 1996 vol. 37, No. 3.

Abstract: #3 Dietary Supplementation with Long Chain (LC) PUFAS (n–3, n–6) in Malnourished Children with Chronic Diarrhea, Arava et al, Pediatric Research, vol. 44, No. 4 1998 (Latin–American Society for Pediatric Research, Abstracts for the 35th Annual Meeting).

Abstract: ™21, Polyunsaturated Fatty Acid Composition according Nutrition Human Milk or Formulas, in term and Preterm Infants, Milad et al, Pediatric Research, vol. 44, No. 4 1998 (Latin–American Society for Pediatric Research, Abstracts for the 35th Annual Meeting).

Abstract: 4120 9:45 Visual maturation of term infants fed w3 long chain polyunsatured fatty acid (LCPUFA) supplemented formula, Birch et al Investigative Ophthalmology & Visual Science, Feb. 15, 1996, vol. 37, No. 3.

Progonstic value of visual evoked potentials (VEP) in infants with visual inattentiveness. Iinuma et al, Electroencephalogr Clin Neurophysiol, 1997:104:165–170.

Lower Incidence of Necrotizing Enterocolitis in Infants Feed a Preterm Formula with Egg Phospholipids, Carlson et al, Pediatric Research, vol. 44 No. 4 1998.

Randomised trial of nutrition for preterm infants after discharge, Lucas et al, Arch Dis Child 1992:67:324–327.

Influence of early diet on outcome in preterm infants, Morley et al, Acta Pediatr suppl 1994: 405: 123–126.

Formula supplementation with long–chain polyunsaturated fatty aids: Are there developmental benefits?, Scott et al, Peidatrics 1998: 102(5) p. e59.

A multicenter long–term safety and efficacy trial of preterm formula supplementated with long–chain polyunsaturated fatty acids, Vanderhoof et al, J Pediatr Gastroenteol Nutr. 2000; 30:121–127.

An electrophysiological technique for the assessment of the development of spatial vision, Zemon et al, Optom Vis Sci 1997: 74:708–716.

Lipids in Human Milk, Jensen, LIPIDS, vol. 34 No. 12 1999 pp. 1243–1271.

Growth and Development in Infants, Norman et al., Health Effects of w3 Polyunsaturated Fatty Acids in Seafoods, World Rev Nutr Diet Basel, Karg 1991 vol. 66, pp. 20–25.

Effects of Long–Chain Polyunsaturated Fatty Acids (LCPUFA) on Early Visual Acuity and Mental Development of Preterm Infants, Nov. 1996, Barcelona, Spain.

* cited by examiner

Age, months corrected age

INFANT FORMULAS CONTAINING LONG-CHAIN POLYUNSATURATED FATTY ACIDS AND USES THEROF

This application is related to a provisional patent application No. 60/196,970 filed Apr. 13, 2000, now abandoned, and to co-owned, co-pending application Ser. No. 09/821,368 filed concurrently.

This invention relates to nutritional formulas, specifically enriched infant formulas that contain long chain polyunsaturated fatty acids (LCPs or LC-PUFAs); and to methods of using such formulas to provide enhanced neurological development in infants, specifically in infants born prematurely ("preterm" infants).

BACKGROUND

Whether or not formulas designed for the preterm infant should be supplemented with LCPs, including arachidonic acid ("AA", 20:4n-6) and/or docosahexaenoic acid ("DHA", 22:6n-3) has become one of the most controversial issues in infant nutrition today. Several lines of logic suggest that preterm infants fed infant formulas without AA and DHA may be at increased risk of sub-optimal blood and tissue levels of these fatty acids compared to the term infant. First, DHA accumulation in the brain and retina is most rapid during the last intrauterine trimester, between 25 and 40 weeks' postmenstrual age (Clandinin, et al. 1980; Martinez, 1991) and the early months after birth (Martinez, 1991); hence, the physiologic requirement for DHA is highest during the perinatal period. Second, the supply of AA and DHA to the preterm infant may be limited due to early termination of maternal-to-fetal transfer of those fatty acids. Clandinin, et al. (1980) reported that approximately 80% of intrauterine AA and DHA accumulation occurs during the last intrauterine trimester. Third, supply may also be limited due to immature de novo synthesis of AA and DHA from their dietary essential precursor fatty acids, linoleic (18:2n-6) and α-linolenic (18:3n-3) acids, respectively. While it has been shown that premature infants are capable of de novo synthesis of AA and DHA (Carnielli, et al. 1996; Salem, et al. 1996; Sauerwald, et al. 1996), it is not clear whether these enzymatic pathways are sufficient in the preterm infant to meet the requirements for AA and DHA (Carlson 1997 Indeed results of randomized controlled trials with preterm infants fed formulas containing DHA but no AA have been interpreted by some to suggest more rapid maturation of retinal physiology (Birch, et al. 1993), visual function (Birch, et al. 1993; Carlson et al 1993a, 1996a) and/or neurodevelopment. However, there are also reports of impaired or slower growth in preterm infants fed formula containing DHA but no AA. For example, Carlson, et al. (1992) found slower growth from 4 to 12 months CA, as well as depressed motor development at 12 months CA (Carlson 1993c), in preterm infants fed a preterm formula containing DHA until hospital discharge followed by a term formula supplemented with DHA until 9 months CA. A second study by Carlson, et al. (1996b) also showed slower growth. In this study, preterm infants were fed a preterm formula containing DHA to 2 months CA, and growth deficits were found at 6, 9 and 12 months CA. A third study (Ryan, et al. 1998) showed slower growth in preterm infants fed a preterm formula containing DHA for two months following hospital discharge and then a term formula containing DHA for an additional four months. Growth faltering in male infants was observed at about 3 and 5 months CA.

While early nutrition and growth can be a significant predictor of later development (Hack et al 1991; Morley & Lucas 1994), there is a lack of consensus that the improvements in visual- and neurodevelopment warrant the feeding of DHA at the expense of slower growth. Thus, there remains a need for a solution that provides improved development (visual, neurological and otherwise) without the concomitant slowed growth rate associated with prior art feeding protocols.

Carlson, et al. (1993b) hypothesized that inclusion of AA in DHA-containing formulas would correct the observations of negative growth. To the applicants' knowledge, no prior studies have tested this hypothesis. To do so effectively, a study must examine growth well beyond 2 months corrected age (CA) as it is during this later time period (e.g. at 3, 5, 6, 9 and 12 months CA) that negative growth has been observed in previous studies (Carlson, et al. 1992, 1996b; Ryan, et al. 1999). Schade, et al in WO 98/44917 (published October 1998, claiming priority to U.S. application No. 60/042,366 dated Mar. 27, 1997) describe a study in which DHA and AA were fed to preterm infants in a fortified formula for 28 days or until hospital discharge, whichever was longer, but infants were then switched to a routine term infant formula without AA and DHA and followed only until 4 months CA. This study reports no differences in visual acuity and no adverse growth issues during or through 4 months CA following this short feeding interval. Vanderhoof, et al. (1999; 2000) report a study wherein preterm infants were fed a fortified formula supplemented with DHA and AA until term CA, then were switched to a standard formula supplemented with DHA and AA until 2 months CA. The 1999 paper reports data from the 2 months CA observations, and the 2000 (August) paper presented certain data to 12 months CA. Growth was found to be not different from the control, but reported outcomes did not include any enhanced development.

Importantly, no studies to date have examined the impact of feeding AA- and DHA-containing formula to premature infants for prolonged periods; e.g. to 6, 9 or 12-months CA, the age recommended in the absence of HM for cessation of formula feeding in term infants (American Academy of Pediatrics, 1998). Likewise, applicants' are aware of no studies that have examined the maturation impact of feeding AA and DHA as part of a nutrient-enriched feeding regimen specifically designed for the preterm infant beyond 6-months CA. Lucas, et al. (1992) demonstrated greater linear growth and weight gain among preterm infants fed a nutrient-enriched formula to 9-months CA compared to preterm infants fed formula designed for the term infant, but neither formula contained DHA or AA.

Further, none of the studies to date have made an attempt to control for the possible confounders of home environment and maternal intelligence. Both variables can significantly influence the development of infants.

REFERENCES

The following references are of interest. A brief description of each is found in the background discussion above or elsewhere in the application.

American Academy of Pediatrics Committee on Nutrition. Pediatric Nutrition Handbook ed 4. Elk Grove Village, Ill.: American Academy of Pediatrics, 1998.

AOAC. Official Methods of Analyses, ed 14. Arlington, Va.: AOAC, 1984, sections 28.082–28.085.

Bayley N. Bayley Scales of Infant Development. San Antonio: Psychological Corp. 1993.

Birch E, Birch D, Hoffman D, Hale L, Everett M, Uauy R. Breast-feeding and optimal visual development. J Pediatr Ophthalmol Strabismus. 1993;30:33–38.

Caldwell B, Bradley R. Home Observation for the Measurement of the Environment. Little Rock: University of Arkansas, 1984.

Carlson S E, Werkman S H, Tolley E A. The effect of long-chain n-3 fatty acid supplement on visual acuity and growth of preterm infants with and without bronchopulmonary dysplasia. Am J Clin Nutr. 1996a;63:687–697.

Carlson S E, Werkman S H. A randomized trial of visual attention of preterm infants fed docosahexaenoic acid until 2 months. Lipids. 1996b:31:85–90.

Carlson S E, Werkman S H, Rhodes P G, Tolley E A. Visual-acuity development in healthy, preterm infants: effect of marine-oil supplementation. Am J Clin Nutr. 1993a;58:35–42.

Carlson S E, Werkman S H, Peeples J M. Arachidonic acid status correlates with first year growth of preterm infants. Proc Natl Acad Sci USA. 1993b:90:1073–1077.

Carlson S E, Lipid Requirements of VLBW infants for Optimal Growth and Development, in Lipids, Learning and the Brain; Fats in Infant Formula, Report of the 103$^{rd}$ Ross Conference on Pediatric Research, Columbus, Ohio. Ross Laboratories. 1993c.

Carlson S E, Cooke R J, Werkman S H, Tolley E A. First year growth of preterm infants fed standard compared to marine oil n-3 supplemented formula. Lipids. 1992;27:901–907.

Carnielli V P, Wattimena D J, Luijendijk I H, Boerlage A, Degenhart H J, Sauer P J. The very low birth weight premature infant is capable of synthesizing arachidonic and docosahexaenoic acids from linoleic and linolenic acids. Pediatr Res. 1996;40:169–174.

Clandinin M R, Chappell J E, Leong S, Heim T, Swyer P R, Chance G W. Intrauterine fatty acid accretion rates in human brain: implications for fatty acid requirements. Early Human Dev. 1980;4:121–9

Clandinin M R, Chappell J E, U.S. Pat. No. 4,670,285

Colombo J, Mitchell D W, Horowitz F D. Infant visual attention in the paired-comparison paradigm: Test-retest and attention-performance relations. Child Dev. 1988;59:1198–1210.

Connor W E, Adamkin D, Auestad N, Connor S, Groh-Wargo S, Hall R, Jacobs J, Lucas A, Mena P. O'Connor D, Nesin M, Singer L, Szabo J. Evaluation of LCP-Containing Formulas for Preterm Infants, The FASEB Journal 14: Addendum 2000. [abstract; presented April 15–18].

Fagan J F, Singer L T. Infant recognition memory as a measure of intelligence. In, Lipsitt L P (ed): Advances in Infancy Research (Vol. 2). Norwood, H J: Ablex, 1983, pp 31–72.

Faldella G, Bovoni M, Alessandroni R, et al. Visual evoked potentials and dietary long chain polyunsaturated fatty acids in preterm infants. Arch Dis Child. 1996;75:F108–F112.

Fenson L, Dale P S, Reznick J S, et al. MacArthur Communicative Development Inventories: User's Guide and Technical Manual. San Diego: Singular Publishing Group, 1993.

Hack M, Breslau N, Weissman B, Aram D, Klein N, Borawski E. Effect of very low birth weight and subnormal head size on cognitive abilities at school age. N Engl J Med. 1991;325:231–237.

Hakkinen V K, Ignatius J, Koskinen M, Koivikko M J, Ikonen R S, Janas M. Visual evoked potential in high-risk infants. Neuropediatrics. 1987;18:70–74.

Hartmann E E, Zemon V, Buckley S W, Fitzgerlad K M, Gordon J, Montalto M B. Visual evoked potential (VEP) estimates of spatial acuity in 4-month old infants: A new swept-parameter technique. Vision Science and Its Applications: Technical Digest Series, vol 1, 1998.

Iinuma K, Lombroso C T, Matsumiya Y. Prognostic value of visual evoked potentials (VEP) in infants with visual inattentiveness. Electroencephalogr Clin Neurophysiol. 1997;104:165–170.

Jacobson S W, Jacobson J L, Sokol R J, Martier S S, Ager J W. Prenatal alcohol exposure and infant information processing ability. Child Dev. 1993;64:1706–1721.

Jenson R G, Lipids in Human Milk. Lipids, 1999 v34(12):1243–1271.

Kocher L. Guide to Growth Assessment of Infants in Clinical Studies. Ross Products Division, 1991.

Kyle D, et al., U.S. Pat. Nos. 5,374,657, 5,550,156, 5,658,767, 5,397,591, 5,407,957, 5,492,938, and 5,711,983.

Lucas A, Bishop N J, King F J, Cole T J. Randomised trial of nutrition for preterm infants after discharge. Arch Dis Child. 1992;67:324–327.

Martinez M. Developmental profiles of polyunsaturated fatty acids in the brain of normal infants and patients with peroxisomal diseases: Severe deficiency of docosahexaenoic acid in Sellweger's and pseudo-Zellweger's syndromes. World Rev Nutr Diet. 1991;66:87–102

Mayer D L, Dobson V: Grating acuity cards: Validity and reliability in studies of human visual development. In, Dobbing J (ed). Developing Brain and Behavior: The Role of Lipids in Infant Formula. San Diego: Academic Press, Ltd, 1997, pp 253–292.

Morley R, Lucas A. Influence of early diet on outcome in preterm infants. Acta Pediatr Suppl. 1994;405-123–126.

Neuringer M, Adamkin D, Auestad N, Castillo M, Connor W, Fitzgerald K, Hall R, Hartmann E E, Jacobs J, Janowsky J, Lucas A, Mena P, O'Connor D, Nesin M, Singer L, Szabo J, Zemon V. Efficacy of Dietary LCPs for Preterm Infants, The FASEB Journal 14: Addendum 2000. [abstract; presented April 15–18].

O'Connor, et al. Growth, Tolerance and Morbidity of Preterm Infants Fed Exclusively Human Milk, Exclusively Preterm Infant Formula or a Combination of Human Milk and a Preterm Infant Formula Until Term Corrected Age, Pediatr. Res. 45:287A 1999 [abstract presented May 1999].

Ryan A S, Montalto M B, Groh-Wargo S, et al. Effect of DHA-containing formula on growth of preterm infants to 59 weeks postmenstrual age. Am J Hum Biol. 1999;11:457–467.

Salem N Jr, Wegner B, Mena P, Uauy R. Arachidonic and docosahexaenoic acids are biosynthesized fromtheir 18-carbon precursors in human infants. Proc Natl Acad Sci USA. 1996;93:49–54

SAS Institute Inc., SAS/STAT® User's Guide, version 6, ed 4. Cary, NC: SAS Institute, Inc., 1989.

Sauerwald T U, Hachey D L, Jensen C L, et al. Effect of dietary alpha-linoleic acid intake on incorporation of docosahexaenoic and arachidonic acids into plasma phospholipids of term infants. Lipids. 1996;31:S131–S135.

Schade D A, et al., International Patent Publication WO 98/44917 (1998).

Scherjon S, Briet J, Oosting H, Kok J. The discrepancy between maturation of visual-evoked potentials and cognitive outcome at five years in very preterm infants with and without hemodynamic signs of fetal brain-sparing. Pediatrics. 2000;105:285–391.

Scott D T, Janowsky J S, Carroll R E, et al. Formula supplementation with long-chain polyunsaturated fatty acids: Are there developmental benefits? Pediatrics. 1998;102 (5):p e59.

Shinmen, et al. Appl. Microbiol. Biotechnol. 31:11–16 (1989).

Teller D Y, McDonald M A, Preston K, need rest et al. Assessment of visual acuity of infants and children: The acuity card procedure. Dev Med and Child Neurol. 1986;28:779–789.

Uauy R, Hoffman D R, Birch E E, Birch D G, Jameson D M, Tyson J: Safety and efficacy of omega-3 fatty acids in the nutrition of very low birth weight infants: Soy oil and marine oil supplementation of formula. J Pediatr. 1994; 124:612–620.

Vanderhoof J, et al. Evaluation of a long-chain polyunsaturated fatty acid supplemented formula on growth, tolerance and plasma lipids in preterm infants up to 48 weeks postconceptual age. J Pediatr Gastroenterol Nutr. 1999; 29:318–326.

Vanderhoof J, et al. A multicenter long-term safety and efficacy trial of preterm formula supplemented with long-chain polyunsaturated fatty acids. J Pediatr Gastroenterol Nutr. 2000; 30:121–127.

van Hof-van Duin J, Cioni G, Bertuccelli B, Fazzi B, Romano C, Boldrini A. Visual outcome at 5 years of newborn infants at risk of cerebral visual impairment. Dev Med Child Neurol. 1998;40:302–309.

Vohr B, Garcia Coll C, Flanagan P, Oh W. Effects of intraventricular hemorrhage and socioeconomic status on perceptual, cognitive, and neurologic status of low birth weight infants at 5 years of age. J Pediatr. 1992;21:280–285.

Wechsler D. Wechsler Adult Intelligence Scale—Revised. San Antonio: The Psychological Corporation, 1981.

Weistheimer G. Scaling of visual acuity measurements. Arch Ophthalmol. 1987;97:327–330.

Woltil H A, van Beusekom C M, Schaafsma A, Muskiet F A J, Okken A: Long-chain polyunsaturated fatty acid status and early growth of low birth weight infants. Eur J Pediatr. 1998;17:146–152.

Yamada, et al. J. Dispersion Science and Technology, 10(4&5), pp561–579 (1989).

Zemon V, Hartmann E E, Gordon J, Prunte-Glowazki A. An electrophysiological technique for the assessment of the development of spatial vision. Optom Vis Sci. 1997;74:708–716.

Hence, we conducted a comprehensive randomized control trial that was adequately powered to assess the suitability and possible benefits of supplementing nutrient-enriched formulas designed for preterm infants with oils (fish/fungal or egg-DTG/fish, as defined below) containing the LCP's AA and DHA. These nutrient-enriched, LCP-containing formulas were fed for a prolonged period beyond 6-months corrected age; in fact to 12-months corrected age.

SUMMARY OF THE INVENTION

There are several aspects of the present invention, each of which is described in a subsection below. Any aspect may occur in combination with any other aspect. Terms used in this summary are defined elsewhere in this application.

Extended Feeding Regimen; Growth Development

A first aspect of the invention relates to an improved method of providing nutrition to a preterm infant, comprising feeding the infant a nutrient-enriched formula for an extended period, i.e. until at least 6 months CA and preferably until 9 or even 12 months CA. Preferably, the nutrient-enriched formula is supplemented with LCPs, specifically AA and DHA at levels discussed herein. Such feeding regimens may be the exclusive source of caloric intake for the infant, or they may be complemented with human milk initially, and/or with solid foods at later stages, e.g. after about 2 to 4 months CA. In a preferred variation, the method comprises feeding the infant according to a staged regimen, using a Type I nutrient-enriched formula containing DHA and AA until the infant reaches hospital discharge or about term corrected age ("CA"), followed by a Type II nutrient-enriched formula containing DHA and AA until the infant reaches at least 6 and preferably 9 or 12 months CA. Feeding regimens such as those described in the above paragraph may be referred to as "catch-up" feeding regimens, referring to the enhanced neurological development discussed below. A major advantage of such feeding regimens over the prior art is that they do not exhibit the growth inhibition that was previously observed when DHA without AA was fed.

Neurological Development

A second aspect of the invention provides for improved or enhanced neurological development of preterm infants by feeding said infant a nutrient-enriched formula containing DHA and AA until the infant reaches at least 6 months CA. Enhanced neurological development is assessed herein as visual development, motor development and/or language development, each discussed below, as compared to infants not receiving comparable nutrient-enriched formula containing DHA and AA until the infant reaches at least 6 months CA. The feeding until the infant reaches at least 6 months CA may consist of exclusively formula, formula plus human milk, or, after about 2 to 4 months CA, it may include supplemental solid food.

Visual Development

An aspect of the invention is a method for improving the visual development of a preterm infant comprising feeding said infant a nutrient-enriched formula containing DHA and AA until the infant reaches at least 6 months CA. Visual development may be measured by any of several techniques, including Teller Acuity cards, Visual Evoked Potential ("VEP") Acuity and VEP Contrast Sensitivity, as described herein. While some investigators have fed DHA in the prior art and found enhanced visual development, this benefit has been associated with lower growth rates in preterm infants and has caused concern among some investigators about the rationale for adding DHA to infant formulas. In fact, while some countries permit the addition of LCPs to formula, they are still prohibited by the regulatory agencies in the US and Canada, presumably due to safety concerns. The present invention overcomes this problem by demonstrating improved visual development without compromising growth.

Preferably according to the invention, DHA and AA are present in amounts and ratios discussed herein and they are fed in nutrient-enriched formulas, for an extended regimen.

Motor Development

Another aspect of the invention resides in a method for enhancing or accelerating the motor neuro-development of a preterm infant, comprising feeding said infant a nutrient-enriched formula containing DHA and AA until the infant reaches at least six months CA, preferably until nine or even 12 months CA. This method appears to be most evident in small preterm infants having birthweights of less than about 1400 g, preferably less than about 1250 g. It may be preferable to feed preterm infants according to a staged extended regimen as described above. The present invention overcomes the prior art problem by demonstrating the improved motor development without compromising growth.

Language Development

Another aspect of the invention resides in a method for enhancing or accelerating the language development of a preterm infant, comprising feeding said infant a nutrient-enriched formula containing DHA and AA until the infant reaches at least six months CA, preferably until nine or even 12 months CA. It may be preferable to feed preterm infants according to a staged extended regimen as described above. The present invention overcomes the prior art problem by demonstrating the improved language development without compromising growth.

LCP/LCP Precursor Balance

Another aspect of the invention is a nutritional composition, such as an infant formula, containing DHA and AA, and their respective precursor essential fatty acids alpha-linolenic acid (ALA) and linoleic acid (LA), in amounts that produce the beneficial effects seen from the present formulas. Through the comprehensive study underlying this invention, it has surprisingly been discovered that much lower levels of DHA and AA may be used in infant formulas to gain the beneficial effects without compromising anthropometric growth. The advantages of lower levels are at least two-fold: First, in view of the growth and safety concerns with DHA and AA noted in the literature, prudence mandates that one add only as much of these LCPs as is necessary to achieve the desired advantages. Second, as these LCP oils are relatively expensive and add significantly to the cost of infant formulas, one should again add only what is necessary. Specific variations of this composition and its use to provide nutrition to preterm infants are discussed herein.

DESCRIPTION OF THE DRAWING FIGURES

Figure 1B:
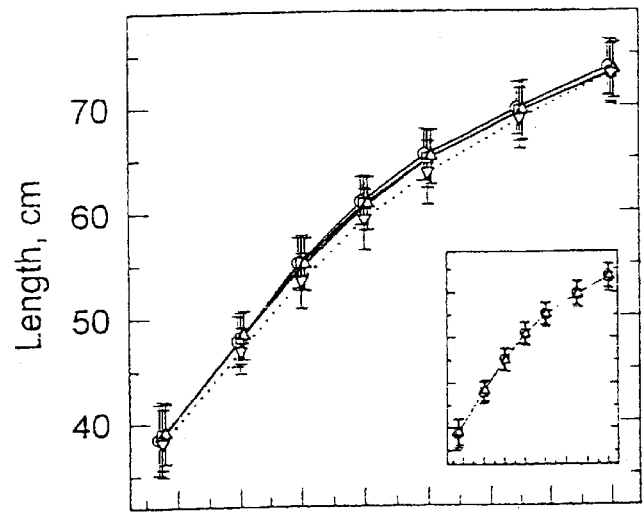
Figure 1C:
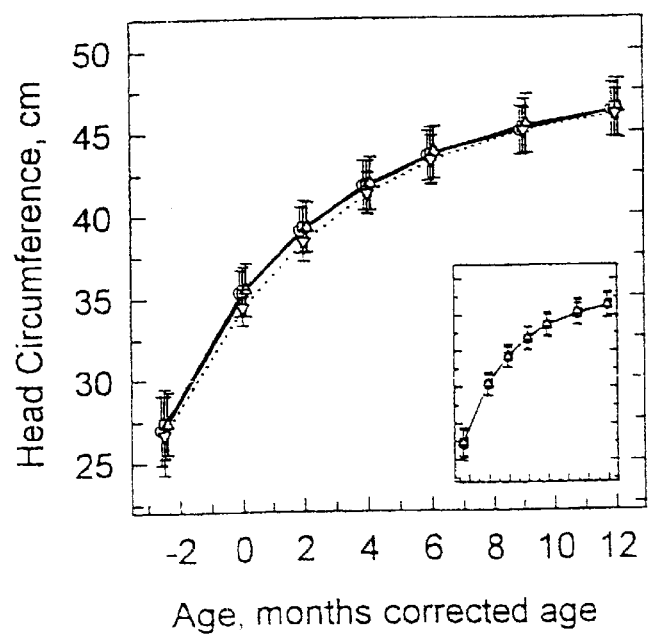

FIGS. 1A to 1C show weight (FIG. 1A), length (FIG. 1B), and head circumference (FIG. 1C) of preterm infants fed human milk and/or nutrient-enriched formula with or without AA and DHA from Study Day 1 (median, 5 days of age) to 12 months CA. Values are presented as mean±SD for the intent-to-treat population (main graphs) and for strict study feeding protocol followers (inset graphs). Hatched lines with triangle symbols denote data for infants who were exclusively human milk fed until term CA. Formula groups: 1) control [Circles], 2) AA+DHA (fish/fungal) [Squares], and 3) AA+DHA (egg-DTG/fish) [Triangles with solid lines].

Figure 2:
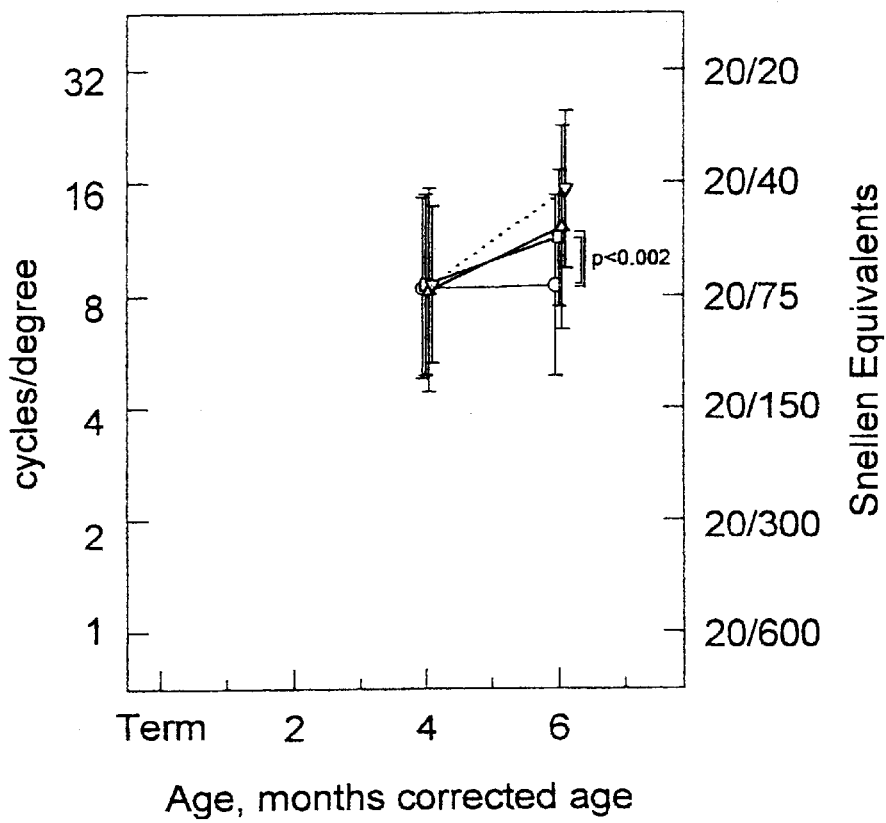

FIG. 2 shows visual development measured by Teller Acuity cards (right axis) at 2, 4 and 6 months CA (±7 days) of preterm infants fed human milk and/or nutrient-enriched formula with or without AA and DHA until 12-months CA. Data for the intent-to-treat population are shown on the left axis as mean (cycles/degree, cy/deg)±SD (octaves). Hatched lines with triangle symbols denote data for infants who were exclusively human milk fed until term CA. Formula groups: 1) control [Circles], 2) AA+DHA (fish/fungal) [Squares], and 3) AA+DHA (egg-DTG/fish) [Triangles with solid lines].

Figure 3:
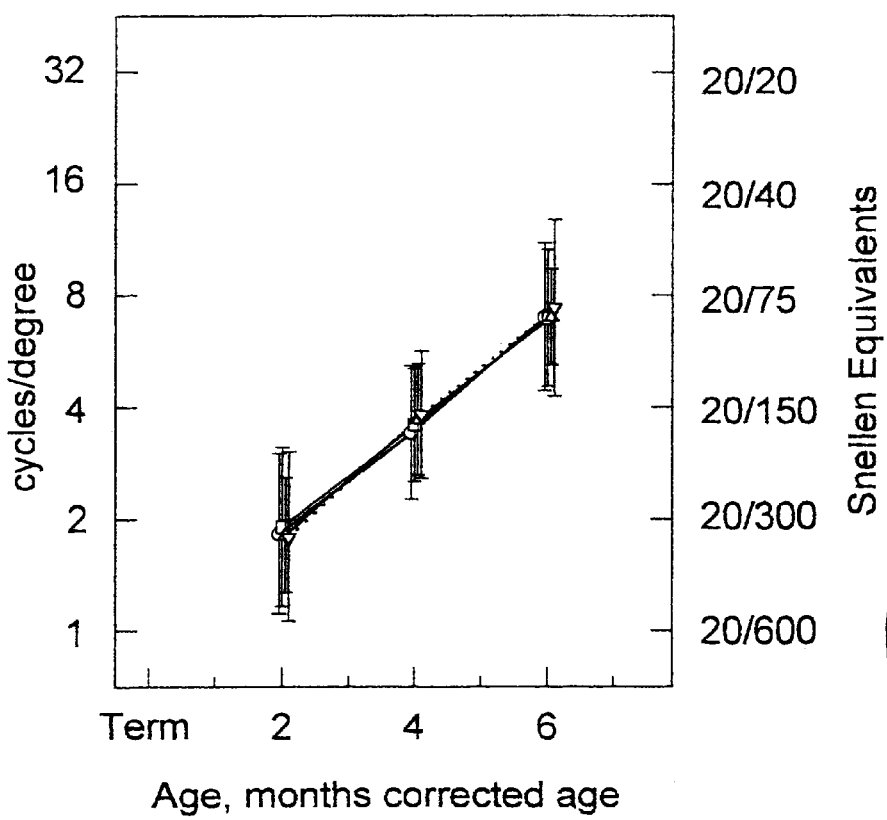

FIG. 3 shows Visual Evoked Potential (VEP) visual acuity (right axis) at 4- and 6-months CA (±7 days) of preterm infants at the Kansas City, New York, and Portland research sites fed human milk and/or nutrient-enriched formula with or without AA and DHA until 12-months CA. Data for the intent-to-treat population are shown on the left axis as mean (cycles/degree, cy/deg)+SD (octaves). Hatched lines with triangle symbols denote data for infants who were exclusively human milk fed until term CA. Formula groups: 1) control [Circles], 2) AA+DHA (fish/fungal) [Squares], 3) AA+DHA (egg-DTG/fish) [Triangles with solid lines]. At 6-months CA, the mean VEP acuity of infants fed the AA+DHA (fish/fungal) (LS means±SE, 11.4+0.1) or AA+DHA (egg-DTG/fish) (12.5±01) formula was greater than that of infants fed the control formula (8.4±0.1).

DETAILED DESCRIPTION

Terminology

Throughout this application, the following terminology and abbreviations may be used.

Fatty acids are an important component of nutrition. Fatty acids are carboxylic acids and are classified based on the length and saturation characteristics of the carbon chain. Short chain fatty acids have 2 to about 6 carbons and are typically saturated. Medium chain fatty acids have from about 6 to about 14 carbons and are also typically saturated. Long chain fatty acids have from 16 to 24 or more carbons and may also be saturated or unsaturated. In longer fatty acids there may be one or more points of unsaturation, giving rise to the terms "monounsaturated" and "polyunsaturated", respectively. Long chain polyunsaturated fatty acids, (LCP's or LC-PUFAs) having 20 or more carbons are of particular interest in the present invention.

LC-PUFAs are categorized according to the number and position of double bonds in the fatty acids according to a nomenclature well understood by the biochemist. There are two series or families of LC-PUFAs, depending on the position of the double bond closest to the methyl end of the fatty acid: the n-3 series contains a double bond at the third carbon, while the n-6 series has no double bond until the sixth carbon. Thus, arachidonic acid ("AA" or "ARA") has a chain length of 20 carbons and 4 double bonds beginning at the sixth carbon. As a result, it is referred to as "20:4 n-6". Similarly, docosahexaenoic acid ("DHA") has a chain length of 22 carbons with 6 double bonds beginning with the third carbon from the methyl end and is thus designated "22:6 n-3". AA and DHA are of particular importance in the present invention. Another important LCP is eicosapentaenoic acid ("EPA") which is designated (20:5 n-3). The biosynthetic pathways for AA (n-6 series) and DHA (n-3 series) from their respective C18 precursors are distinct, but share elongation and desaturation steps and are well understood. Thus, other important LCPs are the C18 fatty acids that are precursors in these biosynthetic pathways, for example, linoleic (18:2 n-6) and γ-linolenic (18:3 n-6) acids in the n-6 pathway, and α-linolenic (18:3 n-3) and stearidonic (18:4 n-3) in the n-3 pathway.

Fatty acids are often found in nature as acyl radicals esterified to alcohols. A glyceride is such an ester of one or more fatty acids with glycerol (1,2,3-propanetriol). If only one position of the glycerol backbone molecule is esterified with a fatty acid, a "monoglyceride" is produced; if two positions are esterified, a "diglyceride" is produced; and if all three positions of the glycerol are esterified with fatty acid a "triglyceride" or "triacylglycerol" is produced. A glyceride is called "simple" if all esterified positions contain the same fatty acid; or "mixed" if different fatty acids are involved. A phospholipid is a special type of diglyceride, wherein the third position on the glycerol backbone is bonded to a nitrogen containing compound such as choline, serine, ethanolamine, inositol, etc., via a phosphate ester. Triglycerides and phospholipids are often classified as long chain or medium chain, according to the fatty acids attached thereto. In human milk, about 98% of the fatty acids are in triglycerides. A "source" of fatty acids may include any of these forms of glycerides from natural or other origins.

Lipids is a general term describing fatty or oily components. In nutrition, lipids provide energy and essential fatty acids and enhance absorption of fat soluble vitamins. The type of lipid consumed affects many physiological parameters such as plasma lipid profile, cell membrane lipid composition and synthesis of mediators of the immune response such as prostagiandins and thromboxanes.

Sources of shorter chain fatty acids useful in the present invention include oils derived from plants, such as borage, black currant seed, corn, coconut, canola, soybean, safflower, high oleic safflower, sunflower, high oleic sunflower, olive, evening primrose, cottonseed, rice bran, grapeseed, flaxseed, garlic, peanuts, almonds, walnuts, wheat germ, and sesame. Such vegetable sources naturally produce fatty acids only to about 18 carbons. Sources of longer LCPs include dairy products like eggs and butterfat; marine oils, such as cod, menhaden, sardine, tuna and many other fish; certain animal fats, lard, tallow and microbial oils such as fungal and algal oils as described in detail in U.S. Pat. No. 5,374,657, 5,550,156, and 5,658,767. Notably, fish oils are a good source of DHA and they are commercially available in "high EPA" and "low EPA" varieties, the latter having a high DHA:EPA ratio, preferably at least 3:1. Algal oils such as those from dinoflagellates of the class Dinophyceae, notably *Crypthecodinium cohnii* are also sources of DHA (including DHASCO™), as taught in U.S. Pat. Nos. 5,397,591, 5,407,957, 5,492,938, and 5,711,983. The genus Mortierella, especially *M. alpina*, and *Pythium insidiosum* are good sources of AA, including ARASCO™ as taught by U.S. Pat. No. 5,658,767 and as taught by Yamada, et al. J. Dispersion Science and Technology, 10(4&5), pp561–579 (1989), and Shirunen, et al. Appl. Microbiol. Biotechnol. 31:11–16 (1989).

Of course, new sources of LCPs may be developed through the genetic manipulation of other organisms, particularly vegetables and/or oil bearing plants. Desaturase and elongase genes have been identified from many organisms and these might be engineered into plant or other host cells to cause them to produce large quantities of LCP-containing oils at low cost. The use of such recombinant oils are also contemplated in the present invention.

Infant formula refers to nutritional formulations that meet the standards and criteria of the Infant Formula Act, (21 USC§350(a) et. seq.) and are intended to replace or supplement human breast milk. Although such formulas are available in at least three distinct forms (powder, liquid concentrate and liquid ready-to-feed ("RTF"), it is conventional to speak of the nutrient concentrations on an "as fed" basis and therefore the RTF is often described, it being understood that the other forms reconstitute or dilute according to manufacturer's directions to essentially the same composition and that one skilled in the art can calculate the relevant composition for concentrated or powder forms.

"Standard" or "Term" infant formula refers to infant formula intended for infants that are born full term as a first feeding. Table A, below, gives some pertinent characteristics of term formula, as well as other types discussed below. The protein, fat and carbohydrate components provide, respectively, from about 8 to 10, 46 to 50 and 41 to 44% of the calories; and the caloric density ranges narrowly from about 660 to about 700 kcal/L (or 19–21 Cal/fl.oz.), usually about 675 to 680 (20 Cal/fl.oz.). The distribution of calories among the fat, protein and carbohydrate components may vary somewhat among different manufacturers of term infant formula. Similarly, other nutrients, such as vitamins, minerals trace minerals and taurine, carnitine and nucleotides vary more widely and therefore are not used as defining characteristics. SIMILAC™ (Ross Products Division, Abbott Laboratories), ENFAMIL™ (Mead Johnson Nutritionals), and GOOD START ™(Carnation) are examples of term infant formula.

By contrast, "nutrient-enriched" formula refers to infant formula that is fortified relative to "standard" or "term" formula. The primary defining characteristic that differentiates nutrient-enriched formulas is the caloric density; a secondary factor is the concentration of protein (see Table A). For example, a formula with a caloric density above about 700 Kcal/L or a protein concentration above about 18 g/L would be considered "nutrient-enriched". Nutrient-enriched formulas typically also contain higher levels of calcium (e.g. above about 650 mg/L) and/or phosphorus (e.g. above about 450 mg/L).

As used herein, there are two types of nutrient-enriched formula. Type I, also known as 'preterm', 'premature' or 'in-hospital' formula, is formula designed to promote growth of the preterm infant at intrauterine rates without disrupting metabolic homeostasis. Type I formulas are characterized by the highest caloric density, typically from about 790 to about 820 kcal/L (or 23–25 Cal/fl.oz.), preferably from about 800 to 810 (24 Cal/fl.oz.). Type I is further differentiated by the higher concentrations of calcium (above about 1200 mg/L, preferably from about 1300 to 1800 mg/L) and phosphorus (above about 600 mg/L, preferably from about 700 to 1000 mg/L). Examples of Type I nutrient-enriched formulas include SIMILAC SPECIAL CARE™ with Iron 24 (Ross Products Division) and ENFAMIL PREMATURE Formula™ with Iron 24 (Mead Johnson).

Type II nutrient-enriched formula, also known as 'post discharge' formula, is intermediate in fortification. For example, Type II formula may have a caloric density ranging from over 700 to nearly 800, preferably from about 740 to 755 Kcal/L; a calcium concentration from 650 to 1200, preferably about 700 to 1000 mg/L; and a phosphorus concentration from 440 to 550, preferably about 440 to 520 mg/L. Low-birth-weight infants and older preterm infants being weaned from a Type I formula are still likely to require a formula that is more energy and nutrient dense than standard term formula. This may occur while hospitalized, following discharge or, more typically, upon discharge from the hospital, Examples of Type II nutrient-enriched formulas include SIMILAC NEOSURE™ (Ross Products Division) and ENFAMIL 22™ (Mead Johnson), recently renamed ENFAMIL ENFACARE™.

TABLE A

Pertinent Characteristics of different types of Infant Formula

| common name<br>Example of comercially<br>available product | Nutrient-enriched<br>Formula (Type I)<br>'preterm' or 'hospital'<br>SIMILAC SPECIAL<br>CARE 24 | Nutrient-enriched<br>Formula (Type II)<br>'post-discharge'<br>SIMILAC NEOSURE | Standard Formula<br>'term'<br>SIMILAC |
|---|---|---|---|
| Caloric Density* kcal/L | 800–810 | 740–755 | 670–680 |
| Caloric distribution: % | | | |
| protein | 10–12 | 9–11 | 9–10 |
| fat | 46–50 | 46–50 | 46–50 |
| carbohydrate | 41–44 | 41–44 | 41–44 |
| Protein Content | | | |
| g/L | 20–26 | 18–22 | 12–18 |
| g/100 Kcal | 2.7–3.2 | 2.5–2.9 | 2.05–2.25 |
| Fat Content | | | |
| g/L | 40–45 | 38–42 | 34–38 |
| g/100 Kcal | 5.0–5.7 | 5.0–5.7 | 5.0–5.7 |
| Carbohydrate Content | | | |
| g/L | 80–90 | 70–85 | 65–80 |
| g/100 Kcal | 10.5–11.4 | 10.1–11 | 10.1–11 |
| Other Features | | | |
| Calcium | | | |
| mg/L | 1300–1800 | 700–1000 | 350–650 |
| mg/100 Kcal | 150–225 | 95–130 | 50–95 |
| Phosphorous | | | |
| mg/L | 700–1000 | 440–520 | 225–500 |
| mg/100 Kcal | 85–125 | 60–70 | 35–75 |

*a defining feature distinguishing Type I from Type II and from Term formula

A nutrient-enriched formula preferably contains LCPs. It has been shown that healthy term infants can make AA and DHA from dietary essential precursor fatty acids, linoleic and α-linolenic acid, respectively. Thus, there appears to be no medical rationale for supplementing term formula with LCPs, provided sufficient precursor essential fatty acids are provided. As a result of the present study, a previously unknown, statistically significant clinical benefit has now been demonstrated in the case of preterm infants, especially very small preterm infants (less than 1250 g). Supplementation of nutrient enriched formula with LCPs should preferably include at least AA and DHA, preferably should not include high levels of EPA. Low EPA fish oils are preferred for this reason if a fish oil source of DHA is employed.

The exact levels of LCP supplementation remains the subject of some discussion. There is wide variation in levels found in human milk depending on diet, stage of lactation and other factors. Jenson (1996, 1999) reported that western women typically had lower milk LCP levels than non-western women. Some proponents advocate supplementing infant formula with DHA and AA levels near the higher end of averages reported for human milk, especially for westerners whose diets typically produce lower average levels. Applicants have found, however, that lower levels of AA and DHA than previously thought may be used while still demonstrating beneficial effects, provided adequate levels of the essential precursor fatty acids and adequate feeding regimens are employed. The biosynthetic pathways of elongation and desaturation that lead to synthesis of LCPs is generally understood and is described in U.S. Pat. No. 5,223,285. Thus it is known that linoleic (18:2n-6, "LA") and intermediates γ-linolenic (18:3n-6, "GLA") and dihomo-γ-linolenic (20:3n-6, "DHGLA") are important precursors to AA (20:4n-6). Similarly, α-linolenic (18:3n-3, "ALA") and intermediates stearodonic (18:4n-3) and EPA (20:5n-3) are important precursors to DHA (22:6n-3).

According to one aspect of the invention, then, levels of DHA and AA and the levels of the respective precursors ALA and LA are interrelated in a somewhat inverse relationship that can be expressed in multiple ways. This has led to the present discovery that lower (hence potentially safer) levels of DHA and AA can be given without loss of the beneficial effects. For example, if minimally effective levels of DHA and AA are present, the ratio of ALA/DHA and the ratios of LA/AA may be used to express the invention. Thus, the levels of DHA and AA as a percent of total fatty acids in a nutrient-enriched composition such as infant formula may stay under about 0.36% and 0.7%, respectively, preferably under 0.3% and 0.5%, respectively, provided the ratio of ALA/DHA ranges from about 4–20, preferably 6–15, and the ratio of LA/AA ranges from about 5–40, preferably about 10–25. In another variation, this inverse relationship may be expressed by specifying maximum levels for the LCPs and minimum levels for the respective precursors. In this way, the invention is expressed by a nutrient-enriched composition having, as a percent (wt/wt) of total fatty acids, not more than about 0.3% DHA and 0.5% AA, while having at least about 2% ALA and 15% LA.

Such compositions according to the invention, while inventive apart from their use, may ideally be used in combination with the feeding regimens described herein to achieve the advantageous developmental effects described herein. Most preferably, the compositions are employed in feeding regimens that achieve the advantageous effects described herein without suffering the normally attendant growth faltering that typically occurs between the 3rd and 12th month CA when preterm infants are fed DHA.

Compositions according to the invention may provide from 100% to about 50% of daily caloric intake. If formula is fed to newborns it may be complemented with some human milk. And as the infant gets to about 2–4 months CA, solid foods often begin to supply some of the calories and the amount of formula may decrease as a percent of total caloric intake.

The level of a particular fatty acid in a formula is typically expressed as percent of the total fatty acids. This percentage multiplied by the absolute concentration of total fatty acids in the formula (either as g/L or g/100 kcal) gives the absolute concentration of the fatty acid of interest (in g/L or g/100 kcal, respectively). Total fatty acids is estimated as about 95% of total fat to account for the weight of the glycerol backbone. Conversion from mg/100 kcal to mg/L is a simple calculation dependant on the caloric density as is known to those skilled in the art. Accordingly, in various preferred and more preferred embodiments, the levels of LCPs in the nutrient-enriched formulas are about the levels set forth in Table B.

skilled in the art can determine what adjustments to make to these ranges to provide the equivalent LCPs to the infant.

Alternatively, suitable levels of these LCP's can be determined on the basis of desired daily intake of the relevant LCPs per kg body weight (see Table C). By one estimate, preterm infants should consume approximately 120 kcal/kg body weight/day until about hospital discharge (typically about term CA) and thereafter approximately 100 kcal/kg body weight/day. Until approximately 2 to 4 months CA, the sole source of these calories is typically human milk, a formula, preferably a Type I or II nutrient-enriched formula, or both. Around 2 to 4 months CA, infants may begin to get cereals or other solid foods as part of their caloric intake, and it has been estimated that by about 12 months about 60% of the caloric intake comes from milk or formula, the remaining 40% being from other foods. This trend of reduced formula intake over time explains the tapering off of DHA and AA intake over time as shown in Table C. As infants consume more and more solid foods that contain little or no DHA and AA, their daily intake drops. This effect is more pronounced with Type II formula since Type II is more likely

TABLE B

Levels of Select LCPs in Nutrient Enriched Formula

| | Type I Nutrient-Enriched | | | Type II Nutrient-Enriched | | |
|---|---|---|---|---|---|---|
| | Range | Preferred | More Preferred | Range | Preferred | More Preferred |
| as percent fatty acids (wt/wt) | | | | | | |
| AA | 0.2–1.0 | 0.35–0.7 | 0.4–0.5 | 0.2–1.0 | 0.35–0.7 | 0.4–0.5 |
| DHA | 0.15–1.0 | 0.19–0.36 | 0.22–0.3 | 0.1–1.0 | 0.1–0.36 | 0.1–0.2 |
| Linoleic (LA) | 10–30 | 15–25 | 15–20 | 12–30 | 15–25 | 15–20 |
| α-linolenic (ALA) | 1.5–4.0 | 2.0–3.0 | 2.3–2.8 | 1.5–4.0 | 2.0–3.0 | 2.2–2.6 |
| as mg fatty acid/100 kcal formula | | | | | | |
| AA | 10–50 | 18–36 | 20–25 | 10–50 | 18–36 | 20–25 |
| DHA | 5–50 | 9–18 | 11–15 | 3–50 | 5–20 | 5–12 |
| Linoleic (LA) | 500–1550 | 750–1300 | 750–1025 | 600–1550 | 750–1300 | 750–1025 |
| α-linolenic (ALA) | 75–200 | 100–155 | 115–145 | 75–200 | 100–155 | 110–145 |
| as weight ratio | | | | | | |
| LA/AA | 2–75 | 20–60 | 30–50 | 2–75 | 30–65 | 40–60 |
| ALA/DHA | 2–40 | 4–20 | 6–15 | 2–40 | 5–40 | 10–25 |

Even more preferable are formulas having LCPs levels that target approximately the levels described in Table 1b of Example 1. The levels set forth in Table B are premised on a formula having a typical fatty acid content, of from about 34 to 45 g/L as shown in Table A. In the event the overall product fatty acid content deviates from this range, one than Type I to be the formula fed during the time solid foods begin supplying caloric intake. And it also explains why, on average, lower intake levels of both AA and DHA may be found for Type II formula, even though the fortification of AA is preferably the same for both Type I and Type II (compare Table B).

TABLE C

Daily Intake Levels of Select LCPs in Nutrient Enriched Formula

| | Type I Nutrient-Enriched | | | Type II Nutrient-Enriched | | |
|---|---|---|---|---|---|---|
| | Range | Preferred | More Preferred | Range | Preferred | More Preferred |
| As intake AA in mg/kg body weight/day by stage | | | | | | |
| in hospital | 5–65 | 10–35 | 18–24 | 2–50 | — | — |
| at discharge or term CA | 5–65 | 15–50 | 25–40 | 2–50 | — | — |
| at 2 mos CA | 5–65 | — | — | 2–50 | 5–40 | 20–35 |
| at 4 mos CA | 5–65 | — | — | 2–50 | 5–40 | 20–35 |
| at 6 mos CA | 2–65 | — | — | 2–50 | 5–40 | 18–30 |

TABLE C-continued

Daily Intake Levels of Select LCPs in Nutrient Enriched Formula

| | Type I Nutrient-Enriched | | | Type II Nutrient-Enriched | | |
|---|---|---|---|---|---|---|
| | Range | Preferred | More Preferred | Range | Preferred | More Preferred |
| at 9 mos CA | 2–65 | — | — | 2–50 | 2–30 | 15–25 |
| at 12 mos CA | 2–65 | — | — | 2–50 | 2–30 | 10–25 |
| As intake DHA in mg/kg body weight/day by stage | | | | | | |
| in hospital | 2–65 | 8–25 | 11–16 | 1–40 | — | — |
| at discharge or term CA | 2–65 | 10–35 | 15–26 | 1–40 | — | — |
| at 2 mos CA | 2–65 | — | — | 1–40 | 3–20 | 7–14 |
| at 4 mos CA | 2–65 | — | — | 1–40 | 3–20 | 7–14 |
| at 6 mos CA | 2–65 | — | — | 1–40 | 3–18 | 5–12 |
| at 9 mos CA | 2–65 | — | — | 1–40 | 2–15 | 4–10 |
| at 12 mos CA | 2–65 | — | — | 1–40 | 2–14 | 3–10 |
| As intake in mg/kg body weight/day typical composite levels at about term CA | | | | | | |
| AA | 2–65 | 10–50 | 20–40 | 2–50 | 5–40 | 20–35 |
| DHA | 2–65 | 10–35 | 11–26 | 1–40 | 3–20 | 7–14 |
| Linoleic (LA) | 400–2000 | 600–1800 | 900–1500 | 500–2000 | 600–1800 | 900–1500 |
| α-linolenic (ALA) | 50–300 | 50–250 | 100–200 | 50–300 | 50–250 | 100–200 |

Similarly, newborns gradually increase consumption over the first several weeks of life, so it is not surprising that the highest daily intakes are found around the time of discharge or slightly thereafter. Daily LCP intakes plotted over time thus produce broad, arcing curves having maxima. The composite AA, DHA, LA and ALA intake values given in the lower part of Table C are typical from the time of about discharge or term CA until about 2 to 4 months CA. Thereafter, lower intake values, by as much as about 40%, are to be expected in accordance with the invention.

Viewed another way, desired intakes of DHA in mg/kg body weight/day range from about 2 to 65, preferably about 3 to 35, and more preferably about 7 to 26; while desired intakes of AA in mg/kg body weight/day range from about 2 to 65, preferably about 5 to 50 and more preferably about 20 to 40. These broader ranges may be subdivided into ranges specific for Type I and Type II formulas as shown in Table C or below. Intakes in mg/kg/day for DHA from a Type I formula ranges typically from about 5 to 40, preferably about 10 to 30, more preferably about 10 to 20. The dosing in mg/kg/day for DHA from a Type II formula typically ranges from about 2 to 20, preferably about 4 to 12 or 15, more preferably about 6 to 10. And the preferred dosing in mg/kg/day for AA from either a Type I or a Type II formula ranges from about 5 to 90, preferably about 10 to 40, more preferably about 15 to 30. The above dosing ranges are alternatives to those given in Table C.

Throughout this application, where ranges are given as "from about x to y", it is to be understood that "about" modifies both the value x and the value y; and that all values between x and y are implicitly and unambiguously disclosed by such range.

"Term" and "Preterm" as used in this application have reference to the conventional gestational period for humans. Thus, a normal "term" infant is born 37 to 42 weeks post conception, while a "preterm" infant is one born prior to 37 weeks post conception. While actual conception may not be precisely determinable, it can be approximated based on last menstrual cycle and/or on other objective estimates, such as early ultrasound assessments or clinical neonatal assessments such as Ballard's. The choice of which method to use in the event of discrepant results is often a matter of physician or institution preference.

Preterm infants have not had the benefit of the mother's life support system for the full gestational term and consequently have many underdeveloped organs and systems.

Preterm infants play a game of growth and development "catch-up" relative to their full term peers. The concept of "corrected age" (CA) has been used to standardize preterm infants to their full term peers for purposes of comparing their growth and development. For example, a preterm infant born 8 weeks prematurely, reaches "term corrected age" at approximately 2 months chronological age, and at 6 months chronological age may developmentally be equivalent to a 4 month-old term infant. The "catch-up" goal is to achieve a developmental status more like that of chronological-age peers.

Preterm infants often receive nutrition parenterally at first, and many receive human milk for at least some initial period. The "first enteral feeding" as used herein, refers to the first time the infant's gut is exposed to nutritive compositions, including human milk, and may include trophic and other feeds used to prime and condition the gut. It is not uncommon in prior art studies for babies to be "enrolled" only after they are receiving 50% or 100% of their daily caloric intake as formula; i.e. after they have established tolerance to the formula. This has the effect of eliminating from the study any babies that are formula-intolerant for any reason. First enteral feeding as used herein does not rely on having established this tolerance. The "first formula feeding" is the first feeding using an artificial infant formula, rather than human milk. It may or may not be the first enteral feeding.

Key to some aspects of the present invention is a "catch-up" feeding regimen utilizing a nutrient-enriched formula for an extended period of time. The extended period both begins earlier in the infant's life and lasts longer. Feeding a nutrient-enriched formula for the extended period produces improved development in the preterm infants.

Most broadly, this aspect of the invention comprises beginning a nutrient-enriched formula as early as possible, potentially as early as the first enteral feeding (SDAY 1) and continuing it beyond hospital discharge to at least 6 months CA, preferably to at least 9 months CA and most desirably to at least 12 months CA and even beyond. Either a Type I or Type II nutrient-enriched formula may be used, preferably containing LCPs DHA and AA. According to a variant embodiment, a Type I nutrient-enriched formula is fed from first formula feeding, preferably from first enteral feeding, until hospital discharge or about term CA, followed by a second stage using a Type II nutrient-enriched formula until at least 6 months CA, preferably even longer, e.g. 9 or 12 months CA. In accordance with these feeding regimens, it is not uncommon for the infant to consume human milk in addition to the nutrient-enriched formula during early stages of life, and, at later stages, to consume cereals and other semi-solid foods along with the nutrient-enriched formula.

In one surprising finding, the enhanced neurological developments discussed herein were found even though the control group received some intake of DHA and AA via human milk, which was permitted in both the control and experimental groups. This fact would tend to minimize any effect seen, by minimizing differences between groups.

Infant maturation, i.e. growth and development, is assessed in many ways. As used herein, "anthropometric growth" or simply "growth" refers generally to the increase in physical size of the infant and is measured by physical metrics such as weight, length and head circumference. These parameters are discussed further in section 1.3.1. It is important to note that the clinical study forming the basis of this invention enrolled preterm infants that, in general, were smaller than prior art studies. Moreover, certain beneficial effects were seen only in the "small" preterm infants. While "small" is a relative term, particularly when referring to preterm infants, it is used herein to refer to infants with a birth weight of less than 1400 g, preferably less than 1250 g.

In addition to physical "growth", there are other maturation parameters or "developments" that may be assessed in infants, namely neurological. While these neurological developments may rely in part on physiologic maturation, they are treated distinctly from anthropometrics. The main neurological developments studied in infants are: visual development, mental development, motor development and language development, each discussed below. It is notable that the enhanced neurological developments that were observed came without any anthropometric growth inhibition or faltering as was seen in prior studies.

"Visual Development" refers generally to the retinal membranes, optic nerve and vision centers of the brain. It is known that retinal photoreceptor membranes contain the body's highest concentration of DHA, and DHA accumulation in the brain and retina is most rapid during the last intrauterine trimester. Accordingly it has been postulated that preterm infants may require nutritional supplementation with LCPs to make up deficits resulting from reduced in-utero time in the final trimester. Several measures are useful for assessing visual development, including Visual Evoked Potential Acuity or "VEP Acuity" and the Teller Visual Acuity Test. These are described in more detail in section 1.3.3 and 1.3.4 below. A third method is VEP Contrast Sensitivity, which is described in more detail in section 1.3.5.

"Mental Development" refers generally to growth of the brain and neurological system and to the ability of the infant to assimilate and process information. It has mental or cognitive aspects as well as motor aspects. Methods used to assess Mental Development include the Bayley Mental Development Index or "MDI." The Fagan "look" test assesses information processing and is another measure of mental development. "Motor Development" refers to an infant's ability to control and coordinate its muscles to make desired movements—another measure of neurological development. The Bayley Psychomotor Development Index or "PDI" may be used to asses motor skills. Each of these tests is described in greater detail in sections 1.3.6 and 1.3.7 below.

"Language Development" refers to the acquisition and utilization of words, especially vocabulary, and is considered yet another measure of neurological development. Language development can be assessed by several methods, including the MacArthur language/vocabulary test, which is described in greater detail in section 1.3.8 below.

Process of Manufacture

The liquid and powder nutritional products of the present invention can be manufactured by generally conventional techniques known to those skilled in the art. Briefly, three slurries are prepared, blended together, heat treated, standardized, spray dried (if applicable), packaged and sterilized (if applicable).

Liquid Products

A carbohydrate/mineral slurry is prepared by first heating water to an elevated temperature with agitation. Minerals are then added. Minerals may include, but are not limited to, sodium citrate, sodium chloride, potassium citrate, potassium chloride, magnesium chloride, tricalcium phosphate, calcium carbonate, potassium iodide and trace mineral premix. A carbohydrate source, such as one or more of lactose, corn syrup solids, sucrose and/or maltodextrin is dissolved in the water, thereby forming a carbohydrate solution. A source of dietary fiber, such as soy polysaccharide, may also be added. The completed carbohydrate/mineral slurry is held under agitation at elevated temperature until it is blended with the other slurries, preferably for no longer than about twelve hours.

An oil slurry is prepared by combining and heating the basic oil blend. The basic oil blend typically contains some combination of soy, coconut, palm olein, high oleic safflower or sunflower oil and medium chain triglycerides. Emulsifiers, such as diacetyl tartaric acid esters of mono, diglycerides, soy mono, diglycerides, and soy lecithin may be used. Any or all of the oil-soluble vitamins A, D, E (natural R,R,R form or synthetic) and K may be added individually or as part of a premix. Beta carotene, which can function as an in vivo antioxidant, may also be added, as may a stabilizer such as carrageenan. Oils containing specific LCPs important to this invention (e.g. DHA and AA) can be added to the oil slurry. Care must be used with these LCPs since they easily degrade and become rancid. The completed oil slurry is held under agitation until it is blended with the other slurries, preferably for a period of no longer than about twelve hours.

A protein in water slurry is prepared by first heating water to an appropriate elevated temperature with agitation. The protein source is then added to the water with agitation. Typically this protein source is intact or hydrolyzed milk proteins (e.g. whey, casein), intact or hydrolyzed vegetable proteins (e.g. soy), free amino acids and mixtures thereof. In general, any known source of amino nitrogen can be used in this invention. The completed protein slurry is held under agitation at elevated temperature until it is blended with the other slurries, preferably for a period no longer than about two hours. As an alternative, some protein may be mixed in a protein-in-fat emulsion rather than protein-in-water.

The protein in water and carbohydrate/mineral slurries are blended together with agitation and the resultant blended slurry is maintained at an elevated temperature. After a brief delay (e.g. a few minutes), the oil slurry is added to the blended slurry from the preceding step with agitation. As an alternative to addition to the oil blend, the LCP oils can be added directly to the blend resulting from combining the protein, carbohydrate/mineral and oil slurries.

After sufficient agitation to thoroughly combine all constituents, the pH of the completed blend is adjusted to the desired range. The blended slurry is then subjected to deaeration, ultra-high temperature heat treatment, emulsification and homogenization, then is cooled to refrigerated temperature. Preferably, after the above steps have been completed, appropriate analytical testing for quality control is conducted. Based on the analytical results of the quality control tests, and appropriate amount of water is added to the batch with agitation for dilution.

A vitamin solution, containing water soluble vitamins and trace minerals (including sodium selenate), is prepared and added to the processed slurry blend with agitation. A separate solution containing nucleotides is prepared and also added to the processed blended slurry with agitation.

The pH of the final product may be adjusted again to achieve optimal product stability. The completed product is then filled into the appropriate metal, glass or plastic containers and subjected to terminal sterilization using conventional technology. Alternatively, the liquid product can be sterilized aseptically and filled into plastic containers.

Powder Products

A carbohydrate/mineral slurry is prepared as was described above for liquid product manufacture.

An oil slurry is prepared as was described above for liquid product manufacture with the following exceptions: 1) Emulsifiers (mono, diglycerides, lecithin) and stabilizers (carrageenan) typically are not added to powder, 2) In addition to the beta carotene, other antioxidants, such as mixed tocopherols and ascorbyl palmitate, can be added to help maintain the oxidative quality of the product during any subsequent spray drying process, and 3) The specific LCPs important to this invention are added after mixing the slurries, rather than to the oil slurry.

A protein in water slurry is prepared as was described above for liquid product manufacture.

The carbohydrate/mineral slurry, protein in water slurry and oil slurry are blended together in a similar manner as described for liquid product manufacture. After pH adjustment of the completed blend, LCPs are then added to the blended slurry with agitation. Desirably, the LCPs are slowly metered into the product as the blend passes through a conduit at a constant rate just prior to homogenization (in-line blending).

After deaeration, ultra-high temperature heat treatment, emulsification and homogenization, the processed blend may be evaporated to increase the solids level of the blend to facilitate more efficient spray drying. The blend then passes through a preheater and a high pressure pump and is spray dried using conventional spray drying technology. The spray dryed powder may be agglomerated, and then is packaged into metal or plastic cans or foil/laminate pouches under vacuum, nitrogen, or other inert environment.

Variations on any of these manufacturing processes are known to or will be readily apparent to those skilled in the art. It is not intended that the invention be limited to any particular process of manufacture. The full text of all US Patents mentioned herein is incorporated by reference.

EXAMPLE 1

Clinical Study 1.1 Study Sample Selection

Four hundred and seventy preterm infants (<33 weeks' gestational age) with birth weights of 750 to 1805 g were enrolled between October 1996 and January 1998 from Neonatal Intensive Care Units (NICUs) agreeing to collaborate with study investigators located in Cleveland, Ohio.; Kansas City, Mo.; Little Rock, Ark.; London, UK; Louisville, Ky.; Portland, Oreg.; New York, N.Y.; and Santiago, Chile. In order to assess the impact of study feeding on early feeding tolerance, infants were to be enrolled within 72 hours of first enteral feeding (including trophic feeds or water) and enteral feeding needed to be initiated within the first 28 days of life. Singleton and twin births and small-for-gestational age infants were allowed to participate. Infants with serious congenital abnormalities that could affect growth and development or who had undergone major surgery prior to randomization were ineligible to participate. Other exclusion criteria included periventricular/intraventricular hemorrhage>Grade II, maternal incapacity including maternal cocaine or alcohol abuse during pregnancy or concurrent, extracorporeal membrane oxygenation, liquid ventilation, asphyxia resulting in severe and permanent neurological damage, or uncontrolled systemic infection at the time of enrollment. Except for the criterion of enrollment within 72 hours of first enteral feeding in which 8% of subjects were enrolled outside this prescribed window, 99% of study subjects met all stated inclusion and exclusion criteria.

1.2 Experimental Design 1.2.1 Study Formula

Nutrient-enriched formulas containing DHA and AA were prepared according to the general procedures outlined above. The modified versions of SIMILAC SPECIAL CARE (Type I) and SIMILAC NEOSURE (Type II) used in the present study differed from the commercial versions of these products in that they contained nucleotides, had a modified whey to casein ratio (~50:50), and contained β-carotene and natural vitamin E (RRR α-tocopherol) instead of a synthetic version. The NeoSure product also contained an increased proportion of lactose as the carbohydrate. These modifications are set forth in Table 1a.

TABLE 1a

Modifications to Commercial Nutrientenriched Formulas

| | In-Hospital Formula (Type I) | | Post-Discharge Formula (Type II) | |
|---|---|---|---|---|
| | Mean | Range | Mean | Range |
| Nucleotides, mg/L | | | | |
| CMP | 40.1 | 37.6–43.0 | 39.4 | 33.3–46.0 |
| UMP | 18.9 | 17.5–20.4 | 16.8 | 15.3–19.0 |
| AMP | 12.4 | 9–13.8 | 11.2 | 9.6–13.6 |
| GMP | 13.2 | 11.7–15.4 | 13.1 | 11.9–14.3 |
| beta-carotene, mg/L | 0.60 | 0.55–0.64 | 0.5 | 0.43–0.54 |
| Vitamin E, IU/L | 40.2 | 38–42.9 | 30.5 | 28.7–32.4 |

The fat blend in SSC consisted of a mixture of 30% soy, 20% coconut, and 50% medium-chain triglyceride (MCT) oils. The fat blend in NeoSure powder consisted of 28% soy, 20% coconut, 25% MCT, and 27% high-oleic safflower oils. The levels of coconut oil were reduced in the LCP-supplemented formulas to keep total fat content constant. In the LCP-supplemented groups, sources of AA and DHA were added to achieve an average level of 0.42% and 0.26% for the SSC formula and 0.42% and 0.16% for the NeoSure formulas. In one of the SSC-NeoSure formula regimens, fungal oil (SUN-TGA25, from *M alpina*; Suntory LTD; Osaka, Japan) and low-EPA fish oil (DHA to eicosapentaenoic [EPA] ratio 5:1) from DHA-rich tuna oil; Mochida International Co., Ltd.; Tokyo, Japan were added to provide AA and DHA, respectively. In the other LCP-supplemented SSC-NeoSure formula regimen, egg-derived triglycerides ("egg-DTG"—Eastman Chemical Co; Kingsport, Tenn, USA) was used to provide AA and DHA to both formulas and a low-EPA fish oil was used to provide additional DHA to the SSC-formula. The control and study formulas had relevant compositions as shown in Table 1b.

a combination of formula and HM. Hence, the study was designed to accommodate HM feeding and at the time of first formula feeding (SDAY 1), infants could have been 1) EHM-fed, 2) exclusively formula-fed, or 3) fed a combination of HM and formula. The timing and advancement of enteral feeding, the duration of HM feeding, and the decision regarding supplementation of enteral feeding was entirely at the discretion of the medical staff except that the TABLE 1b Mean ± SD Fatty Acid Composition (g/100 g total fatty acids) of the Control, and AA and DHA Supplemented, Nutrient-enriched Formulas

| Fatty Acid | In-Hospital Formula (Type I) | | | Post-Discharge Formula (Type II) | | |
|---|---|---|---|---|---|---|
| | Control | AA + DHA Fish/Fungal | AA + DHA EDT/Fish | Control | AA + DHA Fish/Fungal | AA + DHA EDT/Fish |
| Number of Batches | 3 | 3 | 3 | 5 | 6 | 5 |
| Saturated | | | | | | |
| 12:0 (lauric acid) | 9.4 ± 0.2 | 8.1 ± 0.1 | 5.8 ± 0.3 | 9.5 ± 0.3 | 8.5 ± 0.4 | 6.1 ± 0.4 |
| 14:0 (myristic acid) | 3.6 ± 0.1 | 3.2 ± 0.1 | 2.3 ± 0.1 | 3.7 ± 0.1 | 3.4 ± 0.2 | 2.4 ± 0.2 |
| 16:0 (palmitic acid) | 5.3 ± 0.1 | 5.5 ± 0.1 | 6.4 ± 0.1 | 6.3 ± 0.2 | 6.4 ± 0.1 | 7.4 ± 0.1 |
| 18:0 (stearic acid) | 2.6 ± 0.1 | 2.7 ± 0.1 | 3.4 ± 0.1 | 2.4 ± 0.1 | 2.4 ± 0.0 | 3.2 ± 0.9 |
| Monounsaturated | | | | | | |
| 18:1 (oleic acid) | 8.2 ± 0.5 | 8.4 ± 0.7 | 9.8 ± 0.7 | 28.3 ± 0.6 | 27.9 ± 0.6 | 29.8 ± 0.4 |
| Polyunsaturated | | | | | | |
| 18:2n-6 (linoleic acid "LA") | 16.0 ± 0.9 | 16.8 ± 1.0 | 17.5 ± 0.9 | 19.1 ± 1.1 | 19.5 ± 0.7 | 20.3 ± 0.4 |
| 18:3n-3 (α-linolenic acid "ALA") | 2.4 ± 0.1 | 2.6 ± 0.3 | 2.5 ± 0.3 | 2.4 ± 0.2 | 2.4 ± 0.2 | 2.4 ± 0.2 |
| 20:4n-6 (AA) | ND | 0.43 ± 0.02 | 0.41 ± 0.0 | ND | 0.43 ± 0.01 | 0.41 ± 0.02 |
| 20:5n-3 (EPA) | ND | 0.08 ± 0.01 | ND | ND | ND | ND |
| 22:6n-3 (DHA) | ND | 0.27 ± 0.04 | 0.24 ± 0.01 | ND | 0.16 ± 0.01 | 0.15 ± 0.02 |
| ratio LA/AA | — | about 40 | about 40 | — | about 50 | about 50 |
| ratio ALA/DHA | — | about 10 | about 10 | — | about 15 | about 15 |
| Protein Level (g/L) | 22.9 | 22.6 | 22.3 | 20.3 | 20.3 | 20.3 |
| Caloric Density (kcal/L) | 806 | 806 | 806 | 746 | 746 | 746 |

Fatty acid levels were determined at the Clinical Chemistry Department, Ross Products Division, Abbott Laboratories.
Abbreviations:
AA = arachidonic acid;
DHA = docosahexaenoic acid;
EDT = egg-DTG = egg-derived triglyceride;
EPA = eicosapentenoic acid;
ND = not detectable.

1.2.2 Study Groups

Following informed written consent from at least one parent or guardian, infants were randomized to one of three study formula groups with or without the added long-chain polyunsaturated fatty acids, AA and DHA; 1) control, 2) AA+DHA (fish/fungal), and 3) AA+DHA (egg-DTG/fish). The day of first enteral feeding under this study is considered Study Day (SDAY) 1. The computer-generated randomization schedule was blocked for site, gender, and birth weight stratum (750–1250 g and 1251–1800 g) using a permuted blocks algorithm. After randomization, subjects were fed HM and/or the assigned in-hospital Type I preterm formula (modified version of Similac Special Care® ready-to-feed [24 kcal/fl oz]; SSC) with or without triglyceride oils containing AA and DHA until their term CA.

At term CA, infants were transitioned to stage 2 and assigned a post-discharge Type II nutrient-enriched formula (modified version of NeoSure® powder [22 kcal/fl oz]) with and without the same sources of AA and DHA and/or HM to 12-months CA. These formulas provided the dietary essential fatty acids, linoleic and α-linolenic acids (16–20% and 2.5% of total fatty acids, respectively).

During the planning phase of this study, it was apparent that most infants in the participating NICUs were neither exclusively formula- nor HM-fed, but rather most were fed enteral feeding goal was >120 kcal/kcal/day. If HM was fed, it was suggested that it be fortified to 22 to 24 kcal/fl oz and provide a minimum protein intake of 2.8 g/kg/d. One implication of this is that infants in the control groups could have received some DHA and AA if they received any human milk. This fact makes the enhanced development findings in the experimental groups even more compelling.

1.3 Measured Parameters 1.3.1 Anthropometric Growth

Weight, length, and head circumference were measured at SDAY 1 according to standardized procedures (Kocher 1991) (±7 d) and term (±7 d), 2- (±7 d), 4- (±7 d), 6- (±7 d), 9- (±7 d) and 12- (±10 d) month CA birth dates. Infants were weighed at least once in-hospital and twice after hospital discharge using an electronic or double-beam balance accurate to either ±10 g (in-hospital) or ±20 g (post-discharge). Recumbent length and head circumference was measured to the nearest 0.1 cm using a length board with a fixed headboard and a movable footboard (Ellard Length Board, Seattle, Wash.) and non-stretchable tape measure (InserTape®, Ross Products Division, Abbott Laboratories, Columbus, Ohio.), respectively. Length and head circumference was measured at least once at each measurement time in-hospital and twice after hospital discharge.

1.3.2 In-Hospital Feeding Tolerance and Clinical Problems

The percentage of infants who had enteral feedings withheld for at least one day, the percentage of infants who had enteral feedings withheld due to gastric residuals, and the number of days to reach full enteral feeding (100 kcal/kg/d), were determined by reviewing the medical records for each infant for each day of initial hospitalization. Likewise, the incidence of suspected necrotizing enterocolitis (NEC), confirmed NEC (x-ray, surgical or postmortem evidence of pneumatosis, intestinal free air or gas in the portal tract, or perforation), suspected systemic infection, confirmed systemic infection (positive blood culture), and chronic lung disease (supplemental oxygen beyond 1-month postnatal or 36 weeks CA) was extracted from medical records.

1.3.3 Behavioral Visual Acuity

Behavioral visual acuity was assessed using the Teller Acuity Card Procedure (Vistech Inc, Dayton, Teller, et al. 1986) at 2-, 4-, and 6-months CA (±7 days). Infants were shown a series of 25.5×51 cm cards with black and white stripes varying in spatial frequency (stripe width) from 38.0–0.32 cycles/cm (a cycle is one black and white stripe) in half-octave steps. One octave is a halving or a doubling of spatial frequency. The finest grating (stripe width) to which the infant showed a consistent fixation response is the visual acuity threshold in cycles/degree with the variance (SD) in octaves. One of every four study infants, and a small cohort of non-study infants prior to the first study infants reaching 2-, 4-, and 6-months CA, were tested by two trained testers at each site to determine reliability; agreement <0.59 octaves was found for 95% of tests and <0.5 octaves for 78% of the tests.

1.3.4 Visual Evoked Potential (VEP) Acuity

Visual acuity was estimated using a VEP procedure (Hartmann, et al., 1998; Zemon et al, 1997) at the Kansas City, New York, and Portland sites only. Infants [45 control, 50 AA+DHA (fish/fungal), 39 AA+DHA (egg-DTG/fish) and 23 exclusive human milk EHM)] were tested at 4- and 6 months CA (±7 days). The electroencephalogram (EEG) was recorded using three gold-cup EEG electrodes attached with water-soluble paste to the surface of the infant's scalp. The electrodes were placed along the midline of the head with the active site at Oz, referenced to the vertex (Cz) and grounded midway between these two locations (Pz). The EEG was amplified, digitized, and stored in a PC computer (gain=20K, bandpass 0.5–100 Hz). Each research site used an ENFANT recording system to generate the stimuli, record the electrophysiological signals and store the data (Neuroscientific Corp, Farmingdale, N.Y.). This PC computer-based system includes optically-isolated differential amplifiers, an analog-to-digital converter, hardware for stimulus generation, and a linearization feature that incorporates look-up-tables to correct for distortions in the visual display. The three sets of equipment were calibrated to yield equivalent responses. The stimulus monitor was a Nokia RGB monitor (non-interlaced frame rate=59.98 Hz) with a mean space-average luminance of 100 cd/M$^2$. Black and white (100% contrast) horizontal square wave gratings (ie, black and white stripes) were presented on the screen and counter-phase reversed at 7.5 Hz. A series of grating patterns were displayed using a swept-parameter technique. Specifically, during a single swept-parameter run (sweep), spatial frequency of the grating was varied in six discrete steps. Each step was approximately one second in duration, and spatial frequency increased in octave intervals throughout the run from low to high (large to small stripes; 0.8, 1.5, 3.0, 6.0, 12.0, 24.0 cyc/d). Infants were seated on a parent's lap in a darkened room at a distance of 114 cm from the stimulus display. The experimenter was able to see the infant and interrupted the trial when the infant looked away from the stimulus and resumed recording when the infant's gaze returned to the screen.

A discrete Fourier transform was performed on each 1 sec epoch of the EEG. The sine and cosine components of the second harmonic response for each corresponding epoch (either 5 or 10 sweeps) were vector-averaged to yield a mean response. Amplitude and phase values were derived from these means. The Tcirc2 statistic was applied to estimate a 95% confidence circle around the mean vector and obtain a signal-to-noise ratio (S:N; Zemon et al 1997). A true response was deemed present when S:N=1. Grating acuity was estimated by linear interpolation between two adjacent points to a S:N=1 (1 point with S:N>1 and the other with S:N<1). The spatial frequency at which S:N=1 was specified as the acuity estimate.

1.3.5 VEP Contrast Sensitivity

Contrast sensitivity was estimated using a VEP procedure at the Kansas City, New York and Portland sites only at 4- and 6-months CA (±7 days). Contrast was defined by the following equation: $C=(L_{max}-L_{min})\div(L_{max}+L_{min})$ where C=contrast, $L_{max}$=maximum luminance of the pattern and $L_{min}$=minimum luminance of the pattern. This procedure was carried out at the same "sitting" as the VEP acuity procedure using the hardware and placement of the electrodes described above. A 7.5 Hz square-wave temporal signal was used to contrast-reverse each of the following spatial frequencies: 15, 30, and 60 cycles/screen which corresponds to 1.5, 3.0 and 6.0 cyc/d at a viewing distance of 114 cm. Spatial frequency was held constant during an 8 second sweep of contrast. Contrast was increased during the sweep at one contrast level per second through the following 8 contrast levels: 0% (throw-away condition), 0.5%, 1%, 2%, 4%, 8%, 16%, 32%, and 64%. Contrast threshold was defined using a similar interpolation procedure as described above. The reciprocal of contrast needed to yield a S:N=1 was defined as the contrast sensitivity measurement. This electrophysiologically determined measure was designed to mimic the behavioral measure which is the reciprocal of the minimum amount of contrast needed by an infant to detect the presence of black and white stripes.

1.3.6 General Neurological Developmental

The Bayley Scales of Infant Development (Psychological Corporation, ed 2., San Antonio, Tex.) were administered at 12-months CA (±10 d) to assess cognitive and motor development (Mental Developmental Index [MDI]; Psychomotor Developmental Index [PDI]; respectively). One out of approximately every 10 study infants (n=41) was videotaped during the administration of the Bayley and these videotapes were scored centrally (Dr R Arendt, Cleveland, Ohio.), independent of the site tester. The average percent agreement on scoring between the site testers and that determined centrally was 91% (range, 71–100%) and 93% (range 73–100%) for the MDI and PDI, respectively.

1.3.7 Information Processing

The Fagan Test of Infant Intelligence (Infantest Corporation, Cleveland, Ohio; Fagan & Singer 1983) was administered at 6- and 9-month CA (f 7 days) to infants who remained on study feeding at the time of the clinic visit. During a familiarization period, a face stimulus was shown until the infant accumulated a predetermined amount of looking time; during the test period the familiar face stimulus was shown concurrently with a novel face stimulus. The amount of looking time spent on each stimulus was recorded (IBM Thinkpad), and "novelty preference", a measure of visual recognition memory (% of total looking time spent looking at the novel stimulus during the test phase; averaged across 10 tests) was computed. In addition, the mean duration looking time, construed as a measure of efficiency of information processing, was computed for the familiarization period by dividing the total looking time by the number of looks averaged across 10 tests (Colombo, et al. 1988; Jacobson, et al. 1993).

1.3.8 Language Development

The Vocabulary checklist from the infant version of the MacArthur Communicative Development Inventories (Fenson, et al. 1993), a standardized parent-report instrument was completed at 9-months CA (±7 days) and 14-months (±10 days) CA. This checklist of words was used to provide information about each child's vocabulary comprehension (words the child understands) at 9- and 14-months CA and vocabulary production (words the child says) at 14-months CA. Percentile scores were computed from gender-specific norms and transformed to standard scores by convention.

1.3.9 Blood Fatty Acid Analyses

If blood was drawn at Study Day (SDAY) land at hospital discharge as part of routine clinical practice, then additional blood was drawn for determination of the fatty acid composition of plasma and the phosphatidyl-choline (PC) and phosphatidyl-ethanolamine (PE) membrane fractions of red blood cells (RBCs). Further, an attempt was made to obtain blood from all study infants who remained on HM and/or study formulas at 4- and 12-months CA for determination of blood fatty acid levels. Blood samples were processed and frozen at −70° C., shipped on dry ice to a central laboratory (Analytical Research and Services, Ross Products Division) for analysis.

1.3.10 Serious and/or Unexpected Adverse Events (SAEs)

A SAE was defined by the study protocol as any experience which occurred during the clinical trail that resulted in death or was life threatening, disabling, required hospital admission, or required intervention to prevent permanent impairment. This definition excluded non-life-threatening emergency room visits. During the initial hospitalization period, the site research teams were instructed not to include SAEs (other than infant death) which were expected in the natural history of the preterm infant but to include SAEs which, in the opinion of the investigator, could be, or were associated with the use of the study product.

Each SAE was reviewed and assigned an alpha-numeric organ system and severity score by a neonatologist (P Pollack, MD) blinded to study feeding groups. Main categories included: 1) death; 2) pulmonary central, autonomic (e.g., apnea, sudden cyanosis); 3) pulmonary parenchymal (e.g., pneumonia, RSV, asthma, wheezing); 4) other serious non-pulmonary disease (e.g., diarrhea, dehydration, emesis, fever, sepsis); and 5) definitely unrelated to study feeding (e.g., laser therapy for retinopathy, hernia repairs).

1.4 Statistical Methods

This was an intent-to-treat study which included all enrolled infants. Because of the anticipated protocol deviations in this high-risk patient population over the ~16-month study period, a subgroup analysis was planned to include data through the last data collection point for which infants strictly adhered to the feeding protocol. This subgroup of infants was defined as those infants who remained in the feeding protocol at term CA and were consuming>80% of milk feedings (study formula, HM, non-study formula, cow's milk) as study formula and/or HM. For example, if an infant discontinued study feedings between the scheduled 4- and 6-month CA visits, study data at the 4-month CA visit would be included in this subgroup analysis but data collected at the 6-month CA visit would not.

A sample size (n=420) was estimated for a detection of a 0.5 standard deviation (SD) difference with power of 80% and $\alpha$=0.05 in the BSID at 12-months CA among study formula groups in the intent-to-treat analysis. This estimate included an increase in sample size to account for anticipated infant attrition (20%), a possible blunting effect of HM intake on outcome variables (25%) and the formation of an EHM intake during the early neonatal period reference.

Categorical variables were analyzed using Chi-square or Cochran-Mantel-Haenszel test and continuous variables were by analysis of variance (ANOVA) and/or analysis of covariance (ANCOVA). Data obtained at more than one time point were analyzed by repeated-measures analyses. As defined a priori, statistical comparisons among the three study formula groups included a random block for site (ie, site was used as a covariate). In addition, all analyses with continuous outcome variables included the design strata covariates (gender and birthweight [750–1250 g or 1251–1800 g]) and a covariate for HM intake. Human milk intake was defined as a categorical variable based on the classification of infants at the term CA visit as exclusively human-milk-fed (excluded from statistical analyses), exclusively formula-fed, <50% of in-hospital enteral energy intake from formula and ±50% of in-hospital enteral energy intake from formula. Additional preplanned covariates included size for gestation for growth gestational age, size for gestation, a measure of the quality and quantity of cognitive, social, and, emotional support available to the children in the family environment (HOME Inventory; Caldwell & Bradley 1984), and a proxy measure of maternal intelligence (vocabulary component of the WAIS-R; Weschler 1981) for developmental outcomes and prenatal smoking, in-home smoking at hospital discharge, gestational age, size for gestation, HOME Inventory, and the vocabulary component of the WAIS-R for vision outcomes. All statistical tests were two-tailed and a level of significant was set 0.05 and 0.10 for interactions. In consideration of the multiple comparisons made by visit, birth weight stratum and gender, a Bonferroni adjusted p-value was used as the level of significance as appropriate.

1.5 RESULTS 1.5.1 Study Sample

Three-hundred seventy-six (80%) of the 470 infants enrolled completed the study to 12-months CA. Forty-three infants were classified as EHM feeders during the early neonatal period based on HM intake until term CA. Of the 144 infants in the control group, 126 (88%) and 91 (63%) remained on study feeding at term and 12-months CA, respectively. Similarly, of the 140 infants enrolled in the AA+DHA (fish/fungal) group, 120 (860%) and 89 (64%) remained on study feeding at term and 12-months CA, and of the 143 infants enrolled in the AA+DHA (egg-DTG/fish) group, 126 (880/%) and 91 (64%) remained on study feeding at term and 12-months CA. At term CA, 35%, 28%, and 33% of infants in the control, AA+DHA (fish/fungal) and AA+DHA (egg-DTG/fish) groups, respectively, consumed HM at least once per day. By 4months CA, only 14%, 12%, and 12% of infants in the control, AA+DHA (fish/fungal) and AA+DHA (egg-DTG/fish) groups, respectively, consumed HM. Nineteen (13%), 20 (14%), 11 (8%), and 1 (2%) of infants in the control, AA+DHA (fish/fungal), AA+DHA (egg-DTG/fish), and EHM groups, respectively, discontinued study feeding due to symptoms typically associated with feeding intolerance (primary reason for discontinuation provided by site investigator). During the course of the study, 6, 3, 6 and 0 infants in the control, AA+DHA (fish/fungal), AA+DHA (egg-DTG/fish) and EHM groups died. No study deaths were related to study feeding as judged by the investigator at each site.

1.5.2 Infant and Family Demographics

Infant and family baseline demographics did not differ among study formula groups, with the exception of scores on the HOME Inventory (Tables 2 and 3). Infants □ 1250 g randomized to the control group (LS means±SE, 36.0+0.7) had a higher mean HOME Inventory score than those in the AA+DHA (fish/fungal) group (33.7±0.7, p=0.03). Infants in the >1250 g birth weight stratum randomized to the control (LS means SE, 36.2±0.6; p=0.006) and AA+DHA (fish/fungal) (36.3±0.6, p=0.0.004) groups had higher mean HOME Inventory Scores than did infants in the AA+DHA (egg-DTG/fish) group (33.6±0.7). A marginally statistically significant difference in multiple birth status (twin vs. singleton birth) across the three study formula groups was observed (p=0.054). Approximately 17%, 20%, and 28% of subjects in the control, AA+DHA (fish/fungal), and AA+DHA (egg-DTG/fish) group, respectively, were twins.

TABLE 2

Neonatal and Perinatal Characteristics of the Total Study Population of Preterm Infants - Intent-to-Treat

| Characteristics | Control | AA + DHA (Fish/Fungal) | AA + DHA (Egg-DTG/Fish) | EHM* |
|---|---|---|---|---|
| Birthweight[†], g | 1287 ± 272 | 1305 ± 293 | 1309 ± 286 | 1275 ± 312 |
| No. of Subjects | 142 | 138 | 140 | 43 |
| Gestational Age at Birth[†], wks | 29.6 ± 1.9 | 29.8 ± 2.1 | 29.7 ± 2.0 | 29.7 ± 2.1 |
| No. of Subjects | 143 | 138 | 141 | 43 |
| Size at Birth[‡], n | | | | |
| SGA | 9 | 14 | 14 | 7 |
| AGA | 133 | 124 | 126 | 36 |
| Unknown | 1 | 0 | 1 | 0 |
| Gender[‡], n | | | | |
| Male | 77 | 77 | 77 | 20 |
| Female | 66 | 61 | 64 | 23 |
| Multiple Birth Status[‡], n | | | | |
| Singleton | 119 | 110 | 101 | 39 |
| Twin | 24 | 28 | 40 | 4 |
| Apgar Score[‡] | 8.0 ± 1.4 | 8.0 ± 1.4 | 8.0 ± 1.4 | 8.3 ± 1.2 |
| No. of Subjects | 143 | 136 | 141 | 43 |
| Ethnicity, n | | | | |
| US[‡] | | | | |
| Caucasian | 61 | 59 | 62 | 32 |
| African | 22 | 19 | 28 | 2 |
| Hispanic/Latino | 4 | 2 | 3 | 0 |
| Other | 16 | 17 | 7 | 0 |
| UK[‡] | | | | |
| Caucasian | 20 | 21 | 23 | 9 |
| African | 0 | 1 | 0 | 0 |
| Other | 4 | 0 | 2 | 0 |
| Chile[‡] | | | | |
| Hispanic/Latino | 16 | 19 | 16 | — |
| Study Day 1 | | | | |
| Weight[†], g | 1207 ± 276 | 1208 ± 274 | 1219 ± 279 | 1198 ± 326 |
| No. of Subjects | 142 | 138 | 140 | 43 |
| Length,[†] cm | 38.6 ± 3.1 | 38.9 ± 3.1 | 39.1 ± 2.8 | 38.6 ± 3.1 |
| No. of Subjects | 131 | 130 | 132 | 41 |
| Head Circumference,[†] cm | 27.2 ± 2.0 | 27.3 ± 2.0 | 27.4 ± 1.9 | 27.0 ± 2.2 |
| No. of Subjects | 133 | 129 | 135 | 40 |
| Postnatal Age[†], d | 5.5 ± 3.9 | 5.0 ± 2.9 | 4.6 ± 2.8 | 5.5 ± 2.5 |
| No. of Subjects | 142 | 138 | 140 | 43 |

Values are mean ± SD unless otherwise noted.

*Exclusively human milk-fed during the early neonatal period. Reference group only, these data were not included in the statistical analyses.

[†]Differences across formula groups were assessed by ANCOVA controlling for site, gender, birth weight stratum, feeding*gender, and feeding*birth weight stratum. No statistically significant differences were found.

[‡]Differences across formula groups were assessed using Chi-Square analyses controlling for site.

TABLE 3

Family Characteristics: Intent-to-Treat Analysis

| Characteristics | Control | AA + DHA (Fish/Fungal) | AA + DHA (EDT/Fish) | EHM* |
|---|---|---|---|---|
| Maternal Age[†], yrs | 27.2 ± 6.3 (143) | 27.0 ± 6.3 (138) | 27.0 ± 7.0 (141) | 29.7 ± 5.1 (43) |
| Maternal Education[†] | | | | |
| US, yrs | 12.9 ± 2.4 (99) | 13.1 ± 2.4 (96) | 12.8 ± 2.3 (99) | 15.1 ± 2.0 (34) |
| Chile, yrs | 0.5 ± 1.6 (16) | 10.1 ± 2.2 (19) | 8.8 ± 3.1 (16) | NA |
| UK | | | | |
| None | 9 | 4 | 6 | 1 |
| <3 Level[‡] | 5 | 6 | 2 | 0 |
| >3 Level[§] | 6 | 9 | 12 | 2 |
| A Levels | 1 | 0 | 1 | 2 |
| Degree + | 2 | 3 | 4 | 4 |
| Maternal Smoking During Pregnancy[§], n (%) | | | | |
| Yes | 40 (28.0) | 35 (25.4) | 41 (29.3) | 2 (4.7) |
| No | 103 (72.0) | 103 (74.6) | 99 (70.7) | 41 (95.3) |
| Postnatal Smoking in the Home,[§] n (%) | | | | |
| Yes | 37 (27.4) | 39 (29.1) | 44 (32.1) | 4 (9.5) |
| No | 98 (72.6) | 95 (70.9) | 93 (67.9) | 38 (90.5) |
| Prenatal Care[¶], n (%) | | | | |
| 1st trimester | 119 (83.8) | 115 (83.9) | 114 (80.9) | 42 (97.7) |
| 2nd trimester | 19 (13.4) | 17 (12.4) | 20 (14.2) | 0 (0.0) |
| 3rd trimester or none | 4 (2.8) | 5 (3.6) | 7 (5.0) | 1 (2.3) |
| HOME Inventory Score[†]** | 36.3 ± 5.3 (123) | 35.3 ± 5.5 (127) | 34.8 ± 6.5 (109) | 39.4 ± 3.4 (40) |

TABLE 3-continued

Family Characteristics: Intent-to-Treat Analysis

| Characteristics | Control | AA + DHA (Fish/ Fungal) | AA + DHA (EDT/ Fish) | EHM* |
|---|---|---|---|---|
| Maternal WAIS-R Raw Vocabulary Score[†] | 39.3 ± 12.4 (119) | 37.5 ± 15.0 (126) | 37.0 ± 15.2 (108) | 53.2 ± 8.9 (40) |

Values are mean ± SD (number of subjects) unless otherwise noted.
*Exclusively Human Milk-Fed during the early neonatal period. Reference group only, these data were not included in the statistical analyses.
[†]Differences across study formula groups were assessed by ANCOVA controlling for site, gender, birth weight stratum, feeding*gender, and feeding*birth weight stratum.
[‡]UK education equivalents: <3 Certificate of Secondary Education (CSE) or General Certificate of Secondary Education (GCSE) below C grade or
[§]UK education equivalents: >3 CSEs or any O levels or GCSE grade A–C.
[¶]These data were analyzed using Chi-Square analyses controlling for site.
**A statistically significant feeding*birth weight interaction was found (p = 0.0043) for the HOME Inventory Score. Infants ≦1250 g birth weight stratum randomized to the control group (LS Means ± SE, 36.0 ± 0.7) had higher HOME Inventory scores than those randomized to AA + DHA (fish/fungal) group (LS Means ± SE, 33.7 ± 0.7; p = 0.0285). Infants >1250 g birth weight stratum randomized to the control group (LS Means ± SE 36.2 ± 0.6) had higher HOME Inventory Scores than those randomized to AA + DHA (egg-DTG/fish) (33.6 ± 0.7, p = 0.0059). Infants >1250 g birth weight stratum randomized to AA + DHA (fish/fungal) (36.3 ± 0.6) had higher HOME Inventory Scores than those randomized to AA + DHA (egg-DTG/fish) (33.6 ± 0.7, p = 0.0039).

1.5.3 Growth

In the intent-to-treat population, few and inconsistent differences were found in weight, length, or head circumference gains from SDAY 1 to term, 4-. and 12-months CA or in repeated measures analysis of absolute weight, length and head circumference measurements at SDAY 1, term, 2-, 4-, 6-, 9-, and 12-months CA (see Table 4a and 4b & FIG. 1). Mean length gain from SDAY 1 to 12-months CA was greater among control (LS Mean±SE, 5.95±0.07 mm/wk) versus AA+DHA (fish/fungal) (5.67±0.07 mm/wk) infants<1250 g (p=0.008). Mean head circumference gain from SDAY 1 to term CA was greater among female control versus AA+DHA (egg-DTG/fish) infants (9.1±0.2 vs. 8.4±0.2 mm/wk, p=0.005) and among>1250 g AA+DHA (fish/fungal) versus AA+DHA (egg-DTG/fish) infants from SDAY 1 to term CA (9.0 vs. 8.4 mm/wk, respectively; p=0.004). In contrast, repeated measures analyses of anthropometrics across all study visits demonstrated that the weights and lengths of AA+DHA (egg-DTG/fish) infants were greater than that of control infants at term CA (2906±48 g vs. 2757±50 g, p=0.03; 47.1±0.2 cm vs. 46.5±0.02 cm, p=0.01, respectively). These differences disappeared when analysis of the intent-to-treat population excluded those infants consuming>50% of initial in-hospital energy from HM.

Similarly, few and inconsistent differences were found in anthropometric gains or in repeated measures analyses of anthropometric measurements across study visits in the subgroup analysis (strict feed protocol followers). Mean length gain from SDAY 1 to 4-mo CA was greater among control (LS Mean±SE, 8.68±0.14 mm/wk) vs. AA+DHA (egg-DTG/fish) (8.33±0.14 mm/wk, p=0.04). Mean head circumference gains from SDAY 1 to term CA were greater among female control versus that of AA+DHA (egg-DTG/ fish) infants (9.24±0.2 mm/wk vs. 8.4±0.2 mm/wk, p=0.003).

Table 4b shows the data in summary form with a clearer indication of which parameters were statistically different at what times and among which groups. Table 4b shows how few of the growth parameters were significant. With the exception of length and weight at the earliest measured time point (term CA) in the intent-to-treat analysis, none of the absolute measures were statistically different. In a few cases, the control formula gave higher gains than the study formulas; but this may be explained by the fact that the control group, though randomized, happened to have lower weights on average at term. In general, smaller babies grow at faster rates than larger babies.

TABLE 4a

Weight, Length, and Head Circumference Gains: Intent-to-Treat Analysis

| Characteristics | Control | AA + DHA (Fish/ Fungal) | AA + DHA (EDT/ Fish) | EHM* |
|---|---|---|---|---|
| Weight Gain, g/kg/d | | | | |
| SDay 1 to Term CA | 13.4 ± 1.8 (135) | 13.7 ± 1.9 (134) | 13.3 ± 1.8 (135) | 12.0 ± 1.8 (42) |
| SDay 1 to 4 Months CA | 7.3 ± 0.5 (127) | 7.3 ± 0.5 (126) | 7.2 ± 0.5 (121) | 7.1 ± 0.7 (41) |
| SDay 1 to 12 Months CA | 3.6 ± 0.2 (119) | 3.6 ± 0.2 (123) | 3.5 ± 0.2 (105) | 3.5 ± 0.2 (41) |
| Length Gain, mm/week | | | | |
| SDay 1 to Term CA | 9.8 ± 2.1 (135) | 9.8 ± 2.1 (124) | 9.6 ± 1.9 (125) | 9.1 ± 2.1 (40) |
| SDay 1 to 4 Months CA | 8.4 ± 1.0 (120) | 8.3 ± 0.9 (123) | 8.1 ± 0.9 (113) | 7.9 ± 1.1 (39) |
| SDay 1 to 12 Months CA[†] | 5.7 ± 0.5 (111) | 5.6 ± 0.5 (118) | 5.6 ± 0.4 (100) | 5.7 ± 0.5 (39) |
| Head Circumference Gain, mm/week | | | | |
| SDay 1 to Term CA[§] | 8.7 ± 1.4 (126) | 8.4 ± 1.5 (122) | 8.4 ± 1.4 (131) | 8.0 ± 1.1 (39) |
| SDay 1 to 4 Months CA | 5.5 ± 0.7 (121) | 5.5 ± 0.6 (121) | 5.5 ± 0.6 (116) | 5.5 ± 0.5 (38) |
| SDay 1 to 12 Months CA | 3.1 ± 0.3 (112) | 3.1 ± 0.3 (118) | 3.1 ± 0.3 (103) | 3.1 ± 0.3 (38) |

Values are mean ± SD (number of subjects. Differences across study formula groups were assessed by ANCOVA controlling for site, gender, birth weight stratum, size for gestation, human milk intake, feeding*gender, and feeding*birth weight stratum.
*Exclusively Human Milk-Fed during the early neonatal period. Reference group only, these data were not included in the statistical analyses.
[†]Length gains were greater among ≦1250 g infants in the control vs. AA + DHA (fish/fungal) group (LS means 5.74 vs. 5.67 mm/week, p = 0.0078).
[‡]Head circumference gains were greater among female infants in the control vs. AA + DHA (egg-DTG/fish) groups (LS means 9.1 vs. 8.4 mm/week, p = 0.0039).
[§]Head circumference gains were greater among >1250 g infants in the AA + DHA (fish/fungal) vs. AA + DHA (egg-DTG/fish) group (LS means 9.0 vs. 8.4 mm/week, p = 0.0029).

TABLE 4b

Summary of Anthropometric Results

| | Term CA | 2-Mos CA | 4-Mos CA | 6-Mos CA | 9-Mos CA | 12-Mos CA | Interaction |
|---|---|---|---|---|---|---|---|
| *Intent-to-Treat Analysis* | | | | | | | |
| Gains* | | | | | | | |
| Weight | NS | — | NS | — | — | NS | [a] ≤1250 g birth weight only |
| Length | NS | — | NS | — | — | C[†] > FF[‡a] | [b] Females only |
| Head Circumference | C > EF[$b] | — | NS | — | — | NS | [c] >1250 g birth weight only |
| | FF > EF[c] | | | | | | |
| Absolute Measures | | | | | | | |
| Weight | EF > C | NS | NS | NS | NS | NS | |
| Length | EF > C | NS | NS | NS | NS | NS | |
| Head Circumference | NS | NS | NS | NS | NS | NS | |
| *Evaluation Analysis* | | | | | | | |
| Gains* | | | | | | | |
| Weight | NS | — | NS | — | — | NS | |
| Length | NS | — | C > EF | — | — | NS | |
| Head Circumference | C > EF[d] | — | NS | — | — | NS | [d] Females only |
| Absolute Measures | | | | | | | |
| Weight | NS | NS | NS | NS | NS | NS | |
| Length | NS | NS | NS | NS | NS | NS | |
| Head Circumference | NS | NS | NS | NS | NS | NS | |

*Gains were from SDAY 1 to term CA, SDAY 1 to 4-months CA, and SDAY 1 to 12-months CA.
[†]C, control formula
[‡]FF, AA + DHA (fish/fungal) formula
[$]EF, AA + DHA (egg-DTG)/fish formula
NS, not significant.

1.5.4 In-Hospital Feeding Tolerance and Clinical Problems

In both the intent-to-treat and subgroup analyses, there were no differences among study formula groups with respect to the percentage of infants who had enteral feedings withheld for at least one day, the percentage of infants that had feedings withheld due to gastric residuals, and the number of days to reach full enteral feeding, (Table 5). Likewise, there were no differences among study formula groups in the incidence of chronic lung disease or in suspected or confirmed cases of systemic infection or necrotizing enterocolitis.

TABLE 5

In-Hospital Feeding Tolerance and Clinical Problems: Intent-to-Treat Analysis

| | Control | AA + DHA (Fish/ Fungal) | AA + DHA (EDT/ Fish) | EHM* |
|---|---|---|---|---|
| Number of Subjects | 142 | 138 | 140 | 43 |
| Feedings withheld for at least 1 day, % of infants | 29 | 31 | 31 | 26 |
| Feedings withheld due to gastric residuals, % of infants | 20 | 17 | 16 | 14 |
| Days to reach full enteral feeds (100 kcal/kg/d) | 12.8 ± 14.6 | 12.8 ± 12.1 | 12.5 ± 14.1 | 15.8 ± 18.9* |
| Suspected case of NEC, % of infants | 24 | 23 | 26 | 21 |
| Confirmed cases of NEC, % of infants | 4 | 4 | 3 | 0 |
| Suspected systemic infection, % of infants | 33 | 35 | 39 | 33 |
| Confirmed cases of systemic infection, % of infants | 14 | 15 | 15 | 7 |
| Chronic lung disease, % of infants | 25 | 25 | 22 | 28 |

Differences across study formula groups were evaluated by Cochran-Mantel-Haenzel or survivor analysis (days to full enteral feeding only) statistics controlling for site. No statistically significant differences were found.
*Exclusively Human Milk-Fed during the early neonatal period. Reference group only, these data were not included in the statistical analyses.

1.5.5 Behavioral and VEP Acuity

Behavioral and VEP acuity results (cy/d) were log-transformed according to convention (Weistheimer 1987) before analysis and the geometric mean values (cy/d) are reported with SD in octaves (FIGS. 2 & 3). Regardless of whether the analysis was performed on the intent-to-treat population or on strict feeding protocol followers, no significant effect of study feeding on behavioral acuity was found. In contrast, at 6-mo CA, the mean VEP acuity of infants randomized to either AA+DHA (fish/fungal) (LS means+SE, 11.4±0.1 cy/d) or AA+DHA (egg-DTG/fish) (12.5±0.1 cy/d) was greater than for infants randomized to the control formula (8.4±0.1 cy/d, p=0.01). Further, the mean VEP acuity of infants randomized to the AA+DHA supplemented formulas increased between 4- and 6-months CA but the mean VEP acuity of infants randomized to the control group did not. In the subgroup analysis, the mean VEP acuity of infants fed AA+DHA (egg-DTG/fish) (LS Means±SE, 12.9±0.1 cy/d) was greater than control-fed (8.5±0.1 cy/d) infants at 6-months CA (p=0.002). There was a marginal significant difference showing higher visual acuity among AA+DHA (fish/fungal)-fed infants (10.6±0.1 cy/d) than control infants aged 6-months CA (p=0.08).

While a statistical comparison was not made, the VEP acuity at 6-months CA of infants who received study formula during the early neonatal period was less than that of EHM-fed infants. This difference was most marked among infants fed the unsupplemented control formula.

Results from this trial suggest LCP-supplementation results in improved visual development of preterm infants at 6-months CA as assessed by VEP acuity. At 6-months CA, the mean VEP acuity of infants randomized to either AA+DHA (fish/fungal) or AA+DHA (egg-DTG/fish) was approximately 0.34 and 0.42 octaves greater than that for infants randomized to the control formula. While there are distinctions between VEP and recognition acuity (Mayer & Dobson 1997), the magnitude of this difference corresponds to approximately one line on a Snellen eye chart (ie, 20/70 versus 20/50). Unlike AA+DHA-supplemented infants whose VEP acuity improved between 4- and 6-months CA, the VEP acuity of infants randomized to the control formula did not differ, suggesting a deceleration in the development of the visual system in this latter group of infants.

These results are consistent with the higher VEP acuity (1- and 4-months CA) and the more mature VEP wave latency morphology (3-months CA) among preterm infants supplemented with DHA alone as reported by Birch, et al. (1992) and Faldella, et al. (1996). Similarly, Carlson et al (1993a, 1996a) demonstrated improved visual acuity by the Teller card method among DHA-only-supplemented preterm infants from a high-EPA fish oil source at 2- and 4-months CA and at 2-months CA among healthy preterm infants fed DHA alone from a low-EPA fish oil source. In the present study, no statistically significant differences in visual acuity (by Teller method) were noted among the study groups using preplanned comparisons; however, a post-hoc analysis of Teller acuity results at each measurement time (2-, 4-, and 6-months CA) revealed that at 4-months CA infants fed AA+DHA from the egg-DTG/fish source (LS Means±SE, 1.8±0.1 cy/d) had a statistically higher mean acuity scores than 4-month CA infants fed the control formula (1.7±0.1 cy/d, p=0.0323) The absolute difference, however, is not remarkable. In addition to the benefit to visual development strongly implied from the general consistency of the aforementioned study results, there is a growing body of literature suggesting a correlation between the results of early visual assessment and later motor and cognitive impairment (Hakkinen, et al. 1987; linuma, et al. 1997; van Hof-van Duin, et al. 1998; Vohr et al 1992). These correlations suggest that the early benefit of LCP-supplementation to the visual system could have long term consequences; though, this hypothesis remains untested.

The four previously published peer-reviewed clinical trials demonstrating improved visual development secondary to DHA (without AA) supplementation, also reported slower growth in preterm infants or were not powered sufficiently to detect meaningful differences in growth outcomes (Birch, et al. 1992; Carlson, et al. 1993a; Carlson, et al. 1996b; Faldella, et al. 1996; Uauy, et al. 1994). Carlson et al (1993b) hypothesized that despite adequate intakes of the essential fatty acid, linoleic acid, preterm infants may need a dietary source of AA for optimal growth. In contrast, Woltil, et al. (1998) reported that blood levels of AA among preterm infants were associated with anthropometric measures at 10 days of age but disappeared by 42 days of age, leading this group to conclude that AA status was related to intrauterine but not postnatal growth. Results from the study described, herein, suggest that prolonging the feeding of nutrient enriched formulas in combination with AA+DHA supplementation to at least 6-months CA, and preferably to 12-months CA, provides a mechanism whereby enhanced visual development can be actualized without the undesirable consequence of negative growth. In the present study, few and inconsistent differences were found among the >200 statistical comparisons in weight, length, or head circumference gains from SDAY 1 to term, to 4-, and to 12-months CA or in repeated measures analysis of absolute weight, length and head circumference measurements at SDAY 1, term, 2-, 4-, 6-, 9-, and 12-months CA (FIG. 1, Table 4a and 4b).

1.5.6 VEP Contrast Sensitivity

As summarized in Tables 6 and 7 the mean VEP contrast sensitivity measurements of infants did not differ by study formula group using pre-planned statistical comparisons. However, post-hoc analysis of the 1.5 cyc/d contrast sensitivity at 6-month CA revealed that infants randomized to the AA+DHA (egg-DTG/fish) (LS Means±SE, 12.0±0.1, p=0.0084) and AA+DHA (fish/fungal) (10.0±0.10, p=0.0396) study formula groups had higher mean contrast sensitivity measurements than infants randomized to the control group (5.9±0.1). Only the difference between AA+DHA (egg-DTG/fish) and control remained statistically significant using a Bonferroni adjusted α-level of 0.0167.

TABLE 6

Contrast Sensitivity at 4-Months CA Using a Contrast Sweep (1.5, 3.0, and 6.0 cyc/d) - Intent-to-treat

| Contrast Sweep | Control | AA + DHA (Fish/ Fungal) | AA + DHA (Egg-DTG/ Fish) | EHM[†] |
|---|---|---|---|---|
| 1.5 cyc/d | | | | |
| Mean ± SEM | 8.1 ± 0.1 | 7.9 ± 0.1 | 9.6 ± 0.1 | 10.1 ± 0.1 |
| (SD) | (0.5) | (0.5) | (0.6) | (0.4) |
| Median | 8.9 | 8.7 | 16.5 | 12.7 |
| 1st, 3rd quartile | 3.6, 19.8 | 4.2, 15.7 | 2.8, 29.3 | 6.6, 19.1 |
| n | 39 | 45 | 31 | 23 |
| 3.0 cyc/d | | | | |
| Mean ± SEM | 5.0 ± 0.1 | 4.3 ± 01 | 6.3 ± 0.1 | 5.6 ± 0.1 |
| (SD) | (0.5) | (0.4) | (0.5) | (0.4) |
| Median | 6.2 | 3.8 | 6.2 | 63 |
| 1st, 3rd quartile | 2.1, 11.8 | 2.2, 8.2 | 2.8, 17.1 | 2.7, 9.9 |
| n | 38 | 44 | 30 | 23 |

TABLE 6-continued

Contrast Sensitivity at 4-Months CA Using a Contrast Sweep
(1.5, 3.0, and 6.0 cyc/d) - Intent-to-treat

| Contrast Sweep | Control | AA + DHA (Fish/ Fungal) | AA + DHA (Egg-DTG/ Fish) | EHM[†] |
|---|---|---|---|---|
| 6.0 cyc/d | | | | |
| Mean ± SEM | 1.8 ± 0.1 | 1.5 ± 0.0 | 1.6 ± 0.1 | 1.5 ± 0.1 |
| (SD) | (0.4) | (0.3) | (0.3) | (0.3) |
| Median | 1.0 | 1.0 | 1.0 | 1.0 |
| 1st, 3rd quartile | 1.0, 3.2 | 1.0, 2.0 | 1.0, 1.7 | 1.0, 2.2 |
| n | 37 | 42 | 32 | 22 |

*Contrast sensitivity is the reciprocal of the contrast threshold. These data were log 10 transformed prior to statistical analysis. Mean, median, and 1st & 3rd quartile values are the antilog (geometric mean). SEM and SD are in log units. Differences were determined using ANCOVA controlling for site, gender, birth weight stratum, maternal history of smoking during pregnancy, postnatal smoking in the home, maternal education, and human milk intake. No statistically significant feeding or feeding*visit effects were found.
[†]Exclusively human milk-fed during the early neonatal period. Reference group only, these data were not included in the statistical analyses.

TABLE 7

Contrast Sensitivity at 6-Months CA Using a Contrast Sweep
(1.5, 3.0, and 6.0 cyc/d) - Intent-to-treat

| Contrast Sweep | Control | AA + DHA (Fish/ Fungal) | AA + DHA (Egg-DTG/ Fish) | EHM[†] |
|---|---|---|---|---|
| 1.5 cyc/d | | | | |
| Mean ± SEM | 5.8 ± 0.1 | 11.1 ± 0.1 | 12.7 ± 0.1 | 10.1 ± 0.1 |
| (SD) | (0.6) | (0.4) | (0.4) | (0.6) |
| Median | 7.1 | 11.8 | 14.7 | 16.5 |
| 1st, 3rd quartile | 1.6, 18.2 | 7.0, 21.4 | 8.1, 19.5 | 7.1, 24.6 |
| n | 39 | 47 | 33 | 23 |
| 3.0 cyc/d | | | | |
| Mean ± SEM | 4.9 ± 0.1 | 6.9 ± 0.1 | 7.6 ± 0.1 | 8.7 ± 0.1 |
| (SD) | (0.5) | (0.4) | (0.4) | (0.5) |
| Median | 4.5 | 6.6 | 8.4 | 10.5 |
| 1st, 3rd quartile | 1.9, 12.6 | 3.7, 14.4 | 3.9, 16.4 | 3.2, 25.8 |
| n | 39 | 46 | 32 | 23 |
| 6.0 cyc/d | | | | |
| Mean ± SEM | 2.4 ± 0.1 | 2.8 ± 0.1 | 3.6 ± 0.1 | 3.1 ± 0.1 |
| (SD) | (0.4) | (0.4) | (0.5) | (0.4) |
| Median | 2.2 | 2.6 | 4.7 | 2.9 |
| 1st, 3rd quartile | 1.0, 5.5 | 1.0, 4.8 | 1.0, 7.6 | 1.0, 7.0 |
| n | 39 | 45 | 33 | 22 |

*Contrast sensitivity is the reciprocal of the contrast threshold. These data were log 10 transformed prior to statistical analysis. Mean, median, and 1st & 3rd quartile values are the antilog (geometric mean). SEM and SD are in log units. Differences were determined using ANCOVA controlling for site, gender, birth weight stratum, maternal history of smoking during pregnancy, postnatal smoking in the home, maternal education, and human milk intake. No statistically significant feeding or feeding*visit effects were found.
[†]Exclusively human milk-fed during the early neonatal period. Reference group only, these data were not included in the statistical analyses.

1.5.7 General Development Level

Regardless of whether the statistical analysis of the data included all infants randomized into the study or included only those infants who strictly adhered to the feeding protocol, no differences were found among study formula groups in MDI scores (Table 8). In contrast, a statistically significant feeding*birth weight interaction was observed for PDI scores (p=0.005). The mean PDI score of infants ≦1250 g strictly following the feeding protocol was greater among infants fed AA+DHA (fish/fungal) (LS means+SE, 90.6+4.4) versus control (81.8+4.3; p=0.007). The Bayley PDI measures gross motor abilities such as sitting, walking, standing, stair climbing, and hand and finger fine motor skills. As far as we are aware, this is the first prospective randomized trial demonstrating an improvement in motor development scores with AA+DHA supplementation.

The percentage of subjects in the intent-to-treat or subgroup populations who had significantly delayed mental or motor performance did not differ statistically by study formula group. For example, in the intent-to-treat population, approximately 4 and 12% of infants had MDI and PDI scores, respectively, <70, a level described as indicative of significantly delayed performance.

1.5.8 Language

Vocabulary comprehension did not differ among the three study formula groups at either 9- or 14-months CA in either the intent-to-treat or subgroup analysis (Table 8). Likewise, no there were no study feeding differences in vocabulary production at 14-months CA. In these analyses, Spanish-speaking infants and twins were included by computing percentile and gender-specific norms and standard score conversions validated using English-speaking infants (Fenson, et al. 1993). Jackson-Maldonado (1993) reported that the trajectories of language acquisition is similar for Spanish- and English-speaking children, justifying this approach. Nonetheless, when Spanish-speaking infants and twins were removed from the intent-to-treat analysis, infants randomized to the control group (LS means±SE, 94.1±2.9) generally had lower vocabulary comprehension than infants randomized to the AA+DHA (egg-DTG/fish) (102.2±2.8, p=0.0145) or AA+DHA (fish/fungal) groups (100.6±2.9, p=0.0422). Likewise in the evaluable analysis, control-fed infants (LS means±SE, 95.3±3.3) had lower vocabulary comprehension than AA+DHA (egg-DTG/fish)-fed infants (105.4±3.4, p=0.0118).

TABLE 8

Cognitive, Motor, and Language
Development: Intent-to-Treat Analysis*

| Characteristics | Control | AA + DHA (Fish/ Fungal) | AA + DHA (EDT/ Fish) | EHM[†] |
|---|---|---|---|---|
| Bayley's Scales of Infant Development at 12 Months CA | | | | |
| Mental Development Index (MDI) | 92.2 ± 12.2 (119) | 92.8 ± 11.2 (123) | 93.4 ± 13.0 (105) | 93.1 ± 14.5 (41) |
| Psychomotor Development Index (PDI) | 86.3 ± 16.2 (118) | 87.2 ± 14.2 (123) | 85.9 ± 14.4 (105) | 86.8 ± 15.2 (41) |
| MacArthur Communicative Development Inventories Vocabulary Comprehension Scores | | | | |
| 9 Months | 103.7 ± 21.9 (122) | 104.2 ± 19.1 (122) | 101.7 ± 19.4 (102) | 96.2 ± 17.6 (39) |
| 14 Months | 99.9 ± 17.1 (98) | 101.6 ± 16.4 (101) | 101.2 ± 18.8 (93) | 97.0 ± 14.5 (38) |

TABLE 8-continued

Cognitive, Motor, and Language
Development: Intent-to-Treat Analysis*

| Characteristics | Control | AA + DHA (Fish/ Fungal) | AA + DHA (EDT/ Fish) | EHM† |
|---|---|---|---|---|
| Vocabulary Production Scores | | | | |
| 14 Months | 97.8 ± 18.4 (98) | 96.6 ± 17.2 (102) | 98.3 ± 18.1 (93) | 96.6 ± 18.9 (38) |

Values are mean ± SD (number of subjects).
*Differences across formula groups were determined using ANCOVA controlling for: site, gender, birth weight stratum, feeding*gender, feeding*birth weight stratum, HOME, maternal WAIS-R raw vocabulary score, gestational age, size for gestation, human milk intake, birth order, and the first language of the biological mother. MDI and PDI scores <50 were excluded from the statistical analyses but are included in the data presented in this Table. No statistically significant effects of study formula feeding, feeding*gender, or feeding*birth weight stratum were found.
†Exclusively Human Milk-Fed during the early neonatal period. Reference group only, these data were not included in the statistical analyses.

1.5.9 Information Processing

A statistically significant feeding*visit interaction was observed for both novelty preference (p=0.10) and average look duration during the familiarization period (p=0.07), though pairwise comparison of study feeding groups at each time-point yielded differences for novelty preference only (Table 9). The mean novelty preference of AA+DHA (egg-DTG/fish)-fed infants (LS means±SE, 60.0±0.8) was significantly greater than control (57.5±0.8; p=0.02) and AA+DHA (fish/fungal)-fed (56.6±0.8 p=0.003) infants at 6-months CA. The difference between AA+DHA (fish/fungal) and AA+DHA (egg-DTG/fish) remained statistically significant using a Bonferroni adjusted alpha level of 0.0083.

TABLE 9

Fagan Test of Infant Intelligence - Mean ±
SEM (SD) - Evaluable*

| | Control | AA + DHA (Fish/ Fungal) | AA + DHA (Egg-DTG/ Fish) | EHM† |
|---|---|---|---|---|
| % Novelty Preference | | | | |
| 6 Months | 57.5 ± 0.8 (7.4)a,b | 57.0 ± 0.8 (7.5)a | 59.4 ± 0.8 (7.7)b | 57.9 ± 1.1 (7.0) |
| 9 Months | 58.4 ± 0.8 (7.2) | 59.0 ± 0.8 (7.4) | 58.9 ± 0.8 (7.2) | 58.9 ± 1.3 (7.7) |
| Average Look Duration During the Familiarization Phase, sec | | | | |
| 6 Months | 2.2 ± 0.1 (0.8) | 2.2 ± 0.1 (1.0) | 2.1 ± 0.1 (0.8) | 2.2 ± 0.1 (0.8) |
| 9 Months | 1.4 ± 0.0 (0.4) | 1.4 ± 0.0 (0.4) | 1.5 ± 0.1 (0.5) | 1.6 ± 0.1 (0.4) |
| Average Look Duration During the Test Phase, sec | | | | |
| 6 Months | 1.9 ± 0.1 (0.6) | 1.8 ± 0.1 (0.7) | 1.9 ± 0.1 (0.6) | 1.9 ± 0.1 (0.6) |
| 9 Months | 1.3 ± 0.0 (0.3) | 1.3 ± 0.0 (0.4) | 1.3 ± 0.0 (0.4) | 1.3 ± 0.0 (0.3) |
| Average Look Duration for An Abbreviated Time Period of Familiarization, sec‡ | | | | |
| 6 Months | 1.7 ± 0.1 (0.7) | 1.8 ± 0.1 (1.4) | 1.6 ± 0.1 (0.8) | 1.8 ± 0.1 (0.8) |

TABLE 9-continued

Fagan Test of Infant Intelligence - Mean ±
SEM (SD) - Evaluable*

| | Control | AA + DHA (Fish/ Fungal) | AA + DHA (Egg-DTG/ Fish) | EHM† |
|---|---|---|---|---|
| 9 Months | 1.3 ± 0.0 (0.4) | 1.4 ± 0.1 (0.6) | 1.5 ± 0.1 (0.7) | 1.4 ± 0.1 (0.4) |

*Differences across study formula groups were determined using PROC MIXED for repeated measures analysis controlling for site, gender, visit, birth weight stratum, HOME, WAIS-R, gestational age, size for gestation, parity, maternal age, human milk intake, feeding*visit, feeding*gender, and feeding*birth weight stratum. A statistically significant feeding*visit interaction was observed for novelty preference (p = 0.0992), average look duration during an abbreviated time period of familiarization (p = 0.0712). Unlike superscripts in each row denote statistically significant differences using a Bonferroni adjusted α-level of 0.0083.
†Exclusively human milk-fed during the early neonatal period. Reference group only, these data were not included in the statistical analyses.
‡During the First 10 (6 mos CA) or 6 (9 mos CA) Seconds of the First Three Familiarization Periods.

1.5.10 Blood Fatty Acid Analyses

As expected, at SDAY 1, the study formula groups did not differ significantly with respect to the concentration (g/100 g) of AA and DHA in the plasma or in the PE or PC fractions of RBCs (not shown). In contrast, infants consuming either the fish/fungal or egg-DTG/fish formulas had generally higher blood concentrations of AA and DHA in their blood than infants in the control study group at hospital discharge. Infants in the control, fish/fungal, egg-DTG/fish, and EHM groups, had mean (±SD) levels of plasma phospholipid AA (wt%) of 9.9±1.8, 12.0±1.7, 12.5±2.2, and 14.1±2.3, respectively and the mean (±SD) levels of DHA in were 2.6±0.7, 3.4±0.7, 3.3±0.6, and 3.5±0.8, respectively, at hospital discharge.

With the exception of AA levels in RBC PE, statistical analysis of blood fatty acid data at 2- and 4-months CA revealed that infants fed the AA+DHA-supplemented formulas had higher blood levels of AA and DHA in plasma and RBC phospholipids than those fed the control formulas (p<0.0001; Table 10). Infants fed AA+DHA (fish/fungal) but not AA+DHA (egg-DTG/fish) had higher levels of AA in RBC PE than infants fed control formulas (p=0.02).

TABLE 10

Fatty Acid Levels (wt %) in Plasma and Red Blood Cell
Phospholipids at 4- and 12-Months CA - Evaluable Analysis

| | Control | AA + DHA (Fish/ Fungal) | AA + DHA (EDT/ Fish) | EHM* |
|---|---|---|---|---|
| | | Plasma | | |
| 20:4n–6 (AA)† | | | | |
| 4 Month CA | 8.3 ± 1.8 (63) | 12.1 ± 2.0 (64) | 11.8 ± 2.1 (53) | 13.0 ± 1.7 (10) |
| 12 Months CA | 8.6 ± 2.5 (61) | 11.3 ± 2.2 (58) | 11.1 ± 2.3 (51) | 10.6 ± 2.5 (22) |
| 22:6n–3 (DHA)†‡ | | | | |
| 4 Month CA | 2.2 ± 1.0 (63) | 3.9 ± 0.9 (64) | 3.5 ± 0.9 (53) | 4.1 ± 0.8 (10) |
| 12 Months CA | 1.8 ± 0.8 (61) | 3.4 ± 0.8 (58) | 3.1 ± 0.8 (51) | 2.6 ± 0.9 (22) |

TABLE 10-continued

Fatty Acid Levels (wt %) in Plasma and Red Blood Cell
Phospholipids at 4- and 12-Months CA - Evaluable Analysis

|  | Control | AA + DHA (Fish/ Fungal) | AA + DHA (EDT/ Fish) | EHM* |
|---|---|---|---|---|
| Red Blood Cell Phosphatidylethanolamine | | | | |
| 20:4n–6 (AA)$ | | | | |
| 4 Month CA | 17.5 ± 7.1 (67) | 18.7 ± 7.7 (67) | 17.9 ± 7.0 (55) | 18.0 ± 7.0 (15) |
| 12 Months CA | 17.3 ± 6.1 (61) | 18.7 ± 5.9 (58) | 18.5 ± 6.5 (56) | 19.9 ± 5.5 (26) |
| 22:6n–3 (DHA)† | | | | |
| 4 Month CA | 3.2 ± 1.7 (66) | 4.7 ± 2.6 (67) | 4.3 ± 2.3 (55) | 4.1 ± 2.6 (15) |
| 12 Months CA | 2.4 ± 1.1 (61) | 4.2 ± 2.0 (58) | 4.0 ± 1.9 (56) | 4.1 ± 2.2 (26) |
| Red Blood Cell Phosphatidylcholine | | | | |
| 20:4n–6 (AA)† | | | | |
| 4 Month CA | 4.4 ± 1.6 (65) | 5.8 ± 2.5 (65) | 5.6 ± 2.2 (56) | 6.5 ± 2.4 (15) |
| 12 Months CA | 4.2 ± 1.8 (61) | 5.4 ± 2.0 (58) | 5.5 ± 2.0 (56) | 6.0 ± 1.9 (26) |
| 22:6n–3 (DHA)† | | | | |
| 4 Month CA | 0.9 ± 0.4 (60) | 1.4 ± 0.7 (63) | 1.4 ± 0.7 (54) | 1.5 ± 0.9 (15) |
| 12 Months CA | 0.7 ± 0.4 (61) | 1.3 ± 0.6 (58) | 1.1 ± 0.5 (56) | 1.2 ± 0.7 (26) |

Values are mean ± SD (number of subjects). Differences across formula groups were determined using ANCOVA controlling for: site, gender, birth weight stratum, feeding*gender, feeding*birth weight stratum, and feeding*visit.
*Exclusively Human Milk-Fed during the early neonatal period. Reference group only, these data were not included in the statistical analyses.
†Control < AA + DHA (fish/fungal), AA + DHA (egg-DTG/fish), $p < 0.0001$.
‡AA + DHA (egg-DTG/fish) < AA + DHA (fish/fungal), $p < 0.0169$.
$Control < AA + DHA (fish/fungal), $p < 0.0173$.

1.5.11 Serious and/or Unexpected Adverse Events (SAEs)

The percentage of infants who had at least one SAE did not differ among study formula groups with 44%, 46%, 47% of infants randomized to the control, AA+DHA (fish/fungal), AA+DHA (egg-DTG/fish) groups, respectively having at least one SAE. Thirty-eight percent, 39%, and 43% of infants randomized to the control, AA+DHA (fish/fungal) and AA+DHA (egg-DTG/fish) groups, respectively, had at least one hospital readmission. Comparison of the number of SAEs or hospital readmissions did not differ when comparison among feeding groups were made within each birth weight stratum (750–1250 g or 1251–1800 g). Finally, no statistically significant feeding differences were found within each SAE numerical and alphabetical system and severity rating.

We claim:

1. A nutritional composition comprising a nutrient-enriched matrix comprising DHA, AA, ALA and LA in the following amounts as a wt/wt percent of the total fatty acids: DHA up to about 0.36%, AA up to about 0.7%, ALA at least about 2%, and LA at least about 15%.

2. The nutritional composition of claim 1, comprising fatty acids in the following amounts as a wt/wt percent of the total fatty acids: DHA up to about 0.3%, AA up to about 0.5%, ALA at least about 2.2%, and LA at least about 15%.

3. The nutritional composition of claim 1, wherein the ratio of ALA/DHA ranges from about 4 to 40; and the ratio of LA/AA ranges from about 20 to 65.

4. The nutritional composition of claim 1, wherein the ratio of ALA/DHA ranges from about 6 to 25; and the ratio of LA/AA ranges from about 30 to 60.

5. A nutritional composition comprising a nutrient-enriched matrix comprising DHA, AA, ALA and LA, wherein, as a wt/wt percent of the total fatty acids, DHA is present up to about 0.36% and AA is present up to about 0.7%, and wherein the ratio of ALA/DHA ranges from about 4 to 40; and the ratio of LA/AA ranges from about 20 to 65.

6. The nutritional composition of claim 5, wherein, as a wt/wt percent of the total fatty acids, DHA is present from about 0.19 to 0.3% and AA is present from about 0.35 to 0.7%.

7. The nutritional composition of claim 6, wherein the ratio of ALA/DHA ranges from about 6 to 25; and the ratio of LA/AA ranges from about 30 to 60.

8. A method of providing nutrition to a preterm infant comprising feeding said preterm infant a nutritional composition selected from the group consisting of:
   a) a composition comprising a nutrient-enriched matrix comprising DHA, AA, ALA and LA in the following amounts as a wt/wt percent of the total fatty acids: DHA up to about 0.36%, AA up to about 0.7%, ALA at least about 2%, and LA at least about 15%; and
   b) a composition comprising a nutrient-enriched matrix comprising DHA, AA, ALA and LA, wherein, as a wt/wt percent of the total fatty acids, DHA is present up to about 0.36% and AA is present up to about 0.7%, and wherein the ratio of ALA/DHA ranges from about 4 to 40; and the ratio of LA/AA ranges from about 20 to 65.

9. The method according to claim 8 wherein said feeding is continued until the preterm infant reaches a corrected age of about 6 months.

10. The method according to claim 8 wherein said feeding is continued until the preterm infant reaches a corrected age of about 9 months.

11. The method according to claim 8 wherein said feeding is continued until the preterm infant reaches a corrected age of about 12 months.

12. The method according to claim 8 wherein said feeding avoids anthropometric growth inhibition.

13. The method according to claim 8 wherein said nutrient-enriched formula is fed in combination with human milk.

14. A method of providing nutrition to a preterm infant comprising feeding said preterm infant a nutritional composition selected from the group consisting of:
   a) a composition comprising a nutrient-enriched matrix comprising DHA, AA, ALA and LA in the following amounts as a wt/wt percent of the total fatty acids: DHA up to about 0.3%, AA up to about 0.5%, ALA at least about 2.2%, and LA at least about 15%; and
   b) a composition comprising a nutrient-enriched matrix comprising DHA, AA, ALA and LA, wherein, as a wt/wt percent of the total fatty acids, DHA is present up to about 0.36% and AA is present up to about 0.7%, and wherein the ratio of ALA/DHA ranges from about 4 to 40; and the ratio of LA/AA ranges from about 20 to 65.

15. The method according to claim 14 wherein said feeding is continued until the preterm infant reaches a corrected age of about 6 months.

16. The method according to claim 14 wherein said feeding is continued until the preterm infant reaches a corrected age of about 9 months.

17. The method according to claim 14 wherein said feeding is continued until the preterm infant reaches a corrected age of about 12 months.

18. The method according to claim 14 wherein said feeding avoids anthropometric growth inhibition.

19. The method according to claim 14 wherein said nutrient-enriched formula is fed in combination with human milk.

20. The method according to claim 8 wherein said feeding is conducted in two stages: a first stage comprising feeding a Type I nutrient-enriched formula until hospital discharge or about term corrected age; and a second stage comprising feeding a Type II nutrient-enriched formula until about 6 months corrected age.

21. The method according to claim 14 wherein said feeding is conducted in two stages: a first stage comprising feeding a Type I nutrient-enriched formula until hospital discharge or about term corrected age; and a second stage comprising feeding a Type II nutrient-enriched formula until about 6 months corrected age.

22. A nutritional composition comprising a nutrient-enriched matrix comprising each of DHA, AA, ALA and LA in the following amounts as a wt/wt percent of the total fatty acids: DHA up to about 1.0%, AA up to about 1.0%, ALA at least about 1.5%, and LA at least about 10%.

23. The nutritional composition of claim 22, wherein the ratio of ALA/DHA ranges from about 4 to 40; and the ratio of LA/AA ranges from about 20 to 65.

24. The nutritional composition of claim 22, wherein the ratio of ALA/DHA ranges from about 6 to 25; and the ratio of LA/AA ranges from about 30 to 60.

25. A nutritional composition comprising a nutrient-enriched matrix comprising each of DHA, AA, ALA and LA, wherein, as a wt/wt percent of the total fatty acids, DHA is present up to about 1.0% and AA is present up to about 1.0%, and wherein the ratio of ALA/DHA ranges from about 4 to 40; and the ratio of LA/AA ranges from about 20 to 65.

26. The nutritional composition of claim 25, wherein, as a wt/wt percent of the total fatty acids, DHA is present from about 0.10 to 0.36% and AA is present from about 0.35 to 0.7%.

27. The nutritional composition of claim 25, wherein the ratio of ALA/DHA ranges from about 6 to 25; and the ratio of LA/AA ranges from about 30 to 60.

28. A method of providing nutrition to a preterm infant comprising feeding said preterm infant a nutritional composition selected from the group consisting of:

a) a composition comprising a nutrient-enriched matrix comprising each of DHA, M, ALA and LA in the following amounts as a wt/wt percent of the total fatty acids: DHA up to about 1.0%, AA up to about 1.0%, ALA at least about 1.5%, and LA at least about 10%; and b) a composition comprising a nutrient-enriched matrix comprising each of DHA, AA, ALA and LA, wherein, as a wt/wt percent of the total fatty acids, DHA is present up to about 1.0% and AA is present up to about 1.0%, and wherein the ratio of ALA/DHA ranges from about 4 to 40; and the ratio of LA/AA ranges from about 20 to 65.

29. The method according to claim 28 wherein said feeding is continued until the preterm infant reaches a corrected age of about 6 months.

30. The method according to claim 28 wherein said feeding is continued until the preterm infant reaches a corrected age of about 9 months.

31. The method according to claim 28 wherein said feeding is continued until the preterm infant reaches a corrected age of about 12 months.

32. The method according to claim 28 wherein said feeding avoids anthropometric growth inhibition.

33. The method according to claim 28 wherein said nutrient-enriched formula is fed in combination with human milk.

34. The method according to claim 28 wherein said feeding is conducted in two stages: a first stage comprising feeding a Type I nutrient-enriched formula until about hospital discharge or about term corrected age; and a second stage comprising feeding a Type II nutrient-enriched formula until about 6 months corrected age.

35. The method according to claim 28 wherein said nutritional composition further comprises each of DHA, AA, ALA and LA, wherein the ratio of ALA/DHA ranges from about 6 to about 25; and the ratio of LA/AA ranges from about 30 to about 60.

36. The method according to claim 8 wherein said nutritional composition further comprises each of DHA, AA, ALA and LA, wherein the ratio of ALA/DHA ranges from about 6 to about 25; and the ratio of LA/AA ranges from about 30 to about 60.

37. The method according to claim 14 wherein said nutritional composition further comprises each of DHA, AA, ALA and LA, wherein the ratio of ALA/DHA ranges from about 6 to about 25; and the ratio of LA/AA ranges from about 30 to about 60.

38. The nutritional composition of claim 25, wherein said composition is a Type I nutrient enriched formula and wherein the ratio of ALA/DHA ranges from about 4 to about 20; and the ratio of LA/AA ranges from about 20 to about 60.

39. The nutritional composition of claim 38, wherein, as a wt/wt percent of the total fatty acids, DHA is present from about 0.19 to 0.36% and AA is present from about 0.35 to 0.7%.

40. The nutritional composition of claim 25, wherein said composition is a Type II nutrient enriched formula and wherein the ratio of ALA/DHA ranges from about 5 to about 40; and the ratio of LA/AA ranges from about 30 to about 65.

41. The nutritional composition of claim 40, wherein, as a wt/wt percent of the total fatty acids, DHA is present from about 0.10 to 0.36% and AA is present from about 0.35 to 0.7%.

42. The nutritional composition of claim 1, wherein said composition is a Type I nutrient enriched formula and wherein the ratio of ALA/DHA ranges from about 4 to about 20; and the ratio of LA/AA ranges from about 20 to about 60.

43. The nutritional composition of claim 1, wherein said composition is a Type II nutrient enriched formula and wherein the ratio of ALA/DHA ranges from about 5 to about 40; and the ratio of LA/AA ranges from about 30 to about 65.

44. The nutritional composition of claim 5, wherein said composition is a Type I nutrient enriched formula and wherein the ratio of ALA/DHA ranges from about 4 to about 20; and the ratio of LA/AA ranges from about 20 to about 60.

45. The nutritional composition of claim 5, wherein said composition is a Type II nutrient enriched formula and wherein the ratio of ALA/DHA ranges from about 5 to about 40; and the ratio of LA/AA ranges from about 30 to about 6.

* * * * *